(12) United States Patent
Puder et al.

(10) Patent No.: US 9,295,662 B2
(45) Date of Patent: Mar. 29, 2016

(54) METHODS FOR ENHANCING, IMPROVING, OR INCREASING FERTILITY OR REPRODUCTIVE FUNCTION

(71) Applicants: Children's Medical Center Corporation, Boston, MA (US); The General Hospital Corporation, Boston, MA (US)

(72) Inventors: Mark Puder, Medfield, MA (US); Deepika Nehra, Boston, MA (US); Bo R. Rueda, Windham, NH (US)

(73) Assignees: Children's Medical Center Corporation, Boston, MA (US); The General Hospital Corporation, Boston, MA (US)

(*) Notice: Subject to any disclaimer, the term of this patent is extended or adjusted under 35 U.S.C. 154(b) by 0 days.

(21) Appl. No.: 14/383,269

(22) PCT Filed: Mar. 7, 2013

(86) PCT No.: PCT/US2013/029553
§ 371 (c)(1),
(2) Date: Sep. 5, 2014

(87) PCT Pub. No.: WO2013/134482
PCT Pub. Date: Sep. 12, 2013

(65) Prior Publication Data
US 2015/0025048 A1    Jan. 22, 2015

Related U.S. Application Data

(60) Provisional application No. 61/607,884, filed on Mar. 7, 2012, provisional application No. 61/695,510, filed on Aug. 31, 2012.

(51) Int. Cl.
*A61K 31/56* (2006.01)
*A61K 31/202* (2006.01)
*A23L 1/30* (2006.01)
*A61K 45/06* (2006.01)
*A61K 31/232* (2006.01)
*A61K 31/593* (2006.01)

(52) U.S. Cl.
CPC ............ *A61K 31/202* (2013.01); *A23L 1/3008* (2013.01); *A61K 31/232* (2013.01); *A61K 31/593* (2013.01); *A61K 45/06* (2013.01); *A23V 2002/00* (2013.01)

(58) Field of Classification Search
USPC .......................................... 514/168, 560, 547
See application file for complete search history.

(56) References Cited

U.S. PATENT DOCUMENTS

| 8,652,508 B2 * | 2/2014 | Puder et al. ................... 424/439 |
| 2002/0150607 A1 | 10/2002 | Schramm et al. |
| 2008/0226746 A1 * | 9/2008 | Squashic et al. ............... 424/630 |

FOREIGN PATENT DOCUMENTS

| EP | 1304369 | 4/2003 |
| WO | 99/66877 | 12/1999 |
| WO | 03/017945 | 3/2003 |

OTHER PUBLICATIONS

Selesniemi, Aging Cell 7(5):622-629 (2008). "Moderate caloric restriction initiated in rodents during adulthood sustains function of the female reproductive axis into advanced chronological age."
Selesniemi et al., Aging (Albany NY) 1(1):49-57 (2008). "Young adult donor bone marrow infusions into female mice postpone age-related reproductive failure and improve offspring survival."
Selesniemi et al., Proc Natl Acad Sci U S A. 108(30):12319-24 (2011). "Prevention of maternal aging-associated oocyte aneuploidy and meiotic spindle defects in mice by dietary and genetic strategies."
Niikura et al., Aging (Albany NY) 2(12):999-1003 (2010). "Systemic signals in aged males exert potent rejuvenating effects on the ovarian follicle reserve in mammalian females."
Baird et al., Hum Reprod Update 11(3):261-76 (2005). "Fertility and ageing."
Genius, SJ, BJOB 115(1):1-4 (2008). "A Fishy Recommendation: Omega-3 fatty acid intake in preganancy."
Hammiche, Fertility and Sterility 95:1820-1823 (2011). "Increased preconception omega-3 polyunsaturated fatty acid intake improves embyro morphology."

* cited by examiner

*Primary Examiner* — Rei-Tsang Shiao
(74) *Attorney, Agent, or Firm* — Nixon Peabody LLP

(57) ABSTRACT

The present disclosure is directed to methods for enhancing, improving or increasing fertility or reproductive function. For example, the present disclosure is directed to a method for enhancing, improving, or increasing a female human's likelihood of becoming pregnant comprising: administering to the human a nutritional, dietary, or food fatty acid supplement comprising: at least 30% docosahexaenoic acid (DHA), by weight of the total fatty acids in the supplement in a form chosen from ethyl ester, free fatty acid, and triglyceride.

36 Claims, 11 Drawing Sheets

METHODS FOR ENHANCING, IMPROVING, OR INCREASING FERTILITY OR REPRODUCTIVE FUNCTION

CROSS-REFERENCE TO RELATED APPLICATIONS

This application is a 35 U.S.C. §371 National Phase Entry Application of International Application No. PCT/US2013/029553 filed Mar. 7, 2013, which designates the U.S., and which claims benefit under 35 U.S.C. 119(e) of U.S. Provisional Application No. 61/695,510, filed Aug. 31, 2012, and U.S. Provisional Application No. 61/607,884, filed Mar. 7, 2012, all of which are incorporated herein by reference in their entireties.

GOVERNMENT SUPPORT

This invention was made with Government support under grant DK007754 by the National Institutes of Health. The Government has certain rights in this invention.

BACKGROUND

Women approaching advanced maternal age may have poor outcomes with both natural and assisted fertility (see e.g., Wen et al. Fertility and Sterility 2012). Moreover, the incidence of chromosomal abnormalities and birth defects increases with age. As of yet, there is no effective and practical strategy for delaying ovarian aging or improving oocyte quality.

Fertility in women is known to precipitously decline after the age of 35 (Schwartz D, Mayaux M J (1982), Female fecundity as a function of age: results of artificial insemination in 2193 nulliparous women with azoospermic husbands. Federation CECOS. *N Engl J. Med.* 306, 404-406), with fecundity being all but lost by the age of 45 (Ventura S J, Abma J C, Mosher W D, Henshaw S (2004). Estimated pregnancy rates for the United States, 1990-2000: an update. *Natl Vital Stat Rep.* 52, 1-9). With advancements in medical care, a woman's life expectancy has been prolonged by as much as 30 years over the past century while the age of menopause has changed by a meager 3-4 years during this same time period (Soules M R, Bremner W J (1982), The menopause and climacteric: endocrinologic basis and associated symptomatology. *J Am Geriatr Soc.* 30, 547-561). With this, an anomaly has been created in which the reproductive lifespan of women has become strikingly short in the context of overall lifespan, a discrepancy that is more pronounced today than ever before. The modern trend of postponing childbearing in this era of increased longevity, most notable in Western societies, brings the age-related decline in fertility to the forefront of scientific challenges in the field of reproductive medicine (Martin J A, Hamilton B E, Sutton P D, Ventura S J, Mathews T J, Kirmeyer S, Osterman M J (2010). Births: final data for 2007. *Natl Vital Stat Rep.* 58, 1-85).

Biologically, the age at which menopause occurs is determined by the progressive decline and ultimate depletion of the ovarian oocyte-containing follicle reserve (Hansen J P (1986). Older maternal age and pregnancy outcome: a review of the literature. *Obstet Gynecol Surv.* 41, 726-742; Faddy M J, Gosden R G, Gougeon A, Richardson S J, Nelson J F (1992). Accelerated disappearance of ovarian follicles in mid-life: implications for forecasting menopause. *Hum Reprod.* 7, 1342-1346; Tilly J L (2001). Commuting the death sentence: how oocytes strive to survive. *Nat Rev Mol Cell Biol.* 2, 838-848) concomitant with the diminishing quality of oocytes evidenced by an increase in chromosomal and spindle abnormalities and mitochondrial dysfunction (Battaglia D E, Goodwin P, Klein N A, Soules M R (1996). Influence of maternal age on meiotic spindle assembly in oocytes from naturally cycling women. *Hum Reprod.* 11, 2217-2222; Hunt P A, Hassold T J (2008). Human female meiosis: what makes a good egg go bad? *Trends Genet.* 24, 86-93; Selesniemi K, Lee H J, Muhlhauser A, Tilly J L (2011). Prevention of maternal aging-associated oocyte aneuploidy and meiotic spindle defects in mice by dietary and genetic strategies. *Proc Natl Acad Sci USA.* 108, 12319-12324). These changes significantly contribute to the poor success of natural and assisted fertility attempts for women of advanced reproductive age and to the increased incidence of chromosomal anomalies when conception is successful (Navot D, Bergh P A, Williams M A, Garrisi G J, Guzman I, Sandler B, Grunfeld L (1991b). Poor oocyte quality rather than implantation failure as a cause of age-related decline in female fertility. *Lancet.* 337, 1375-1377; van Kooij R J, Looman C W, Habbema J D, Dorland M, to Velde E R (1996). Age-dependent decrease in embryo implantation rate after in vitro fertilization. *Fertil Steril.* 66, 769-775). Similar to humans, laboratory rodents exhibit an age-related decline in ovarian follicle reserve leading to a state of natural infertility approximately halfway through their chronological lifespan (Gosden R G, Laing S C, Felicio L S, Nelson J F, Finch C E (1983). Imminent oocyte exhaustion and reduced follicular recruitment mark the transition to acyclicity in aging C57BL/6J mice. *Biol Reprod.* 28, 255-260; Perez G I, Robles R, Knudson C M, Flaws J A, Korsmeyer S J, Tilly J L (1999). Prolongation of ovarian lifespan into advanced chronological age by Bax-deficiency. *Nat. Genet.* 21, 200-203; Wu J M, Zelinski M B, Ingram D K, Ottinger M A (2005). Ovarian aging and menopause: current theories, hypotheses, and research models. *Exp Biol Med* (Maywood). 230, 818-828). Aging female mice exhibit many of the physiological changes observed in postmenopausal women, including the loss of cyclic ovarian function, making these animals an ideal in vivo model for the study of ovarian failure. Unfortunately, despite relevant rodent model systems and promising proposed strategies for prolonging the female reproductive lifespan (Perez G I, Robles R, Knudson C M, Flaws J A, Korsmeyer S J, Tilly J L (1999). Prolongation of ovarian lifespan into advanced chronological age by Bax-deficiency. *Nat. Genet.* 21, 200-203; Perez G I, Jurisicova A, Wise L, Lipina T, Kanisek M, Bechard A, Takai Y, Hunt P, Roder J, Grynpas M, Tilly J L (2007). Absence of the proapoptotic Bax protein extends fertility and alleviates age-related health complications in female mice. *Proc Natl Acad Sci USA.* 104, 5229-5234; Selesniemi K, Lee H J, Tilly J L (2008). Moderate caloric restriction initiated in rodents during adulthood sustains function of the female reproductive axis into advanced chronological age. *Aging Cell.* 7, 622-629; Selesniemi K, Lee H J, Niikura T, Tilly J L (2009). Young adult donor bone marrow infusions into female mice postpone age-related reproductive failure and improve offspring survival. *Aging* (Albany N.Y.). 1, 49-57; Niikura Y, Niikura T, Wang N, Satirapod C, Tilly J L (2010). Systemic signals in aged males exert potent rejuvenating effects on the ovarian follicle reserve in mammalian females. *Aging* (Albany N.Y.). 2, 999-1003; Selesniemi K, Lee H J, Muhlhauser A, Tilly J L (2011). Prevention of maternal aging-associated oocyte aneuploidy and meiotic spindle defects in mice by dietary and genetic strategies. *Proc Natl Acad Sci USA.* 108, 12319-12324), an effective and realistic strategy for significantly delaying ovarian aging or improving oocyte quality has yet to be developed.

Changes in the dietary patterns of humans over time may provide insight into novel avenues for delaying ovarian aging. Anthropological and nutritional studies demonstrate a remarkable change in the human diet over the past 100 years, most notably with regard to the type and amount of fat consumed (Eaton S B, Konner M (1985). Paleolithic nutrition. A consideration of its nature and current implications. *N Engl J. Med.* 312, 283-289; Simopoulos A P (1991). Omega-3 fatty acids in health and disease and in growth and development. *Am J Clin Nutr.* 54, 438-463; Simopoulos A P (2003). Importance of the ratio of omega-6/omega-3 essential fatty acids: evolutionary aspects. *World Rev Nutr Diet.* 92, 1-22; Simopoulos A P (2006). Evolutionary aspects of diet, the omega-6/omega-3 ratio and genetic variation: nutritional implications for chronic diseases. *Biomed Pharmacother.* 60, 502-507; Simopoulos A P (2009). Evolutionary aspects of the dietary omega-6:omega-3 fatty acid ratio: medical implications. *World Rev Nutr Diet.* 100, 1-21; Simopoulos A P (2011). Importance of the omega-6/omega-3 balance in health and disease: evolutionary aspects of diet. *World Rev Nutr Diet.* 102, 10-21). These changes are manifested by both an absolute and a relative change in the omega-6 and omega-3 fatty acid consumption. Today, the Western diet provides an omega-6 to omega-3 fatty acid ratio of as high as 25:1, which is in stark contrast to the 1:1 ratio historically consumed by humans (Simopoulos A P (2006). Evolutionary aspects of diet, the omega-6/omega-3 ratio and genetic variation: nutritional implications for chronic diseases. *Biomed Pharmacother.* 60, 502-507), creating a nutritional environment that is different from our ancestors and from which our genetic constitution was selected. This change is particularly relevant given that the shift in dietary habits over the last 100 years is accompanied by a concurrent downward trend in the fertility rates for women over the age of 35 (Baird D T, Collins J, Egozcue J, Evers L H, Gianaroli L, Leridon H, Sunde A, Templeton A, Van Steirteghem A, Cohen J, Crosignani P G, Devroey P, Diedrich K, Fauser B C, Fraser L, Glasier A, Liebaers I, Mautone G, Penney G, Tarlatzis B (2005). Fertility and ageing. *Hum Reprod Update.* 11, 261-276).

It is disclosed herein that the consumption omega-3 fatty acids may prolong murine reproductive function into advanced maternal age, while a diet rich in omega-6 fatty acids may be associated with poor reproductive success at advanced maternal age. Furthermore, even short-term consumption of omega-3 fatty acids initiated at the time of the normal age-related rapid decline in murine reproductive function may be associated with improved oocyte quality, while short-term consumption of omega-6 fatty acids may result in poor oocyte quality. Thus, omega-3 fatty acids may provide an effective and practical avenue for delaying ovarian aging and improving oocyte quality at advanced maternal age.

SUMMARY

The present disclosure relates to a method for enhancing, improving, or increasing a female human's likelihood of becoming pregnant comprising: administering to the human a nutritional, dietary, or food fatty acid supplement comprising: at least 30% docosahexaenoic acid (DHA), by weight of the total fatty acids in the supplement in a form chosen from ethyl ester, free fatty acid, and triglyceride.

The present disclosure also relates to a method of maintaining or improving oocyte and/or ovum quality in a human in need thereof comprising: administering to the human a nutritional, dietary, or food fatty acid supplement comprising: at least 30% docosahexaenoic acid (DHA), by weight of the total fatty acids in the supplement in a form chosen from ethyl ester, free fatty acid, and triglyceride. The oocyte and/or ovum quality may be maintained or improved by decreasing the likelihood of at least one chromosomal abnormality in the oocyte and/or ovum. In at least one embodiment, the human is at least 25 years of age, at least 30 years of age, or at least 35 years of age and may be undergoing fertility treatment.

The present disclosure also relates to a method of treating infertility in a female human in need thereof comprising: administering to the human a pharmaceutical or medical food fatty acid composition comprising: at least 80% docosahexaenoic acid (DHA) in a form chosen from ethyl ester, free fatty acid, and triglyceride, and eicosapentaenoic acid (EPA) in a form chosen from ethyl ester, free fatty acid, and triglyceride, by weight of the total fatty acids in the composition.

The present disclosure also relates to a method of enhancing, improving, or increasing a female human's likelihood of becoming pregnant comprising: administering to the human a nutritional, dietary, or food fatty acid supplement comprising: at least 80% docosahexaenoic acid (DHA) in a form chosen from ethyl ester, free fatty acid, and triglyceride, and eicosapentaenoic acid (EPA) in a form chosen from ethyl ester, free fatty acid, and triglyceride, by weight of the total fatty acids in the supplement.

The present disclosure also relates to a method of enhancing and/or prolonging fertility and/or reproductive function in a female human or animal in need thereof comprising administering to the human or the animal a nutritional, dietary, or food fatty acid supplement comprising: at least 30% docosahexaenoic acid (DHA), by weight of the total fatty acids in the supplement in a form chosen from ethyl ester, free fatty acid, and triglyceride.

The present disclosure also relates to a method of delaying the onset of menopause in a female human or animal in need thereof comprising administering to the human or the animal a nutritional, dietary, or food fatty acid supplement comprising: at least 30% docosahexaenoic acid (DHA), by weight of the total fatty acids in the supplement in a form chosen from ethyl ester, free fatty acid, and triglyceride.

The present disclosure also relates to a method of decreasing the likelihood of birth defects comprising administering to a female human a nutritional, dietary, or food fatty acid supplement comprising: at least 30% docosahexaenoic acid (DHA), by weight of the total fatty acids in the supplement in a form chosen from ethyl ester, free fatty acid, and triglyceride.

The present disclosure also relates to a method of decreasing the likelihood of fetal or infant mortality comprising administering to a female human a nutritional, dietary, or food fatty acid supplement comprising: at least 30% docosahexaenoic acid (DHA), by weight of the total fatty acids in the supplement in a form chosen from ethyl ester, free fatty acid, and triglyceride.

The present disclosure further relates to the use of a composition chosen from a nutritional supplement, a dietary supplement, a food supplement, a pharmaceutical grade supplement, and a medical food, for enhancing, improving, or increasing a female human's likelihood of becoming pregnant, comprising: administering to the human the composition comprising: at least 30% docosahexaenoic acid (DHA), by weight of the total fatty acids in the supplement in a form chosen from ethyl ester, free fatty acid, and triglyceride.

The present disclosure also relates to the use of a composition chosen from a nutritional supplement, a dietary supplement, a food supplement, a pharmaceutical grade supplement, and a medical food, for maintaining or improving oocyte and/or ovum quality in a female human in need thereof, comprising: administering to the human the composition comprising: at least 30% docosahexaenoic acid (DHA), by weight of the total fatty acids in the supplement in a form chosen from ethyl ester, free fatty acid, and triglyceride.

Described herein are methods of prolonging and enhancing fertility. The methods described herein relate to the discovery that consumption of omega-3 fatty acids sufficient to achieve a serum ratio of omega-3 fatty acids to omega-6 fatty acids of from about 1:3 to 3:1 (e.g. about 1:1) increases oocyte quality and prolongs murine reproductive function into advanced maternal age. The implementation of this diet at the time of the normal rapid decline in murine reproductive function results in an improvement in oocyte quality. The methods described herein can be used in both natural and assisted reproduction such as in vitro fertilization. In some embodiments, the methods described herein relate to enhancing or prolonging fertility at advanced maternal age (e.g., menopause). In some embodiments of the present disclosure, the methods can be used to improve oocyte or ovum quality in a female subject. In some embodiments, the methods can be used to prevent or treat abnormalities in spindle integrity or mitochondrial dynamics in the developing oocyte or ovum. In some embodiments, the methods can be used to prevent disorders of chromosomal segregation such as Down Syndrome and other trisomies in the developing oocyte or ovum.

Additional advantages of the present disclosure will be set forth in part in the description which follows, and in part will be obvious from the description, or may be learned by practice of the present disclosure. The advantages of the present disclosure will be realized and attained by means of the elements and combinations particularly pointed out in the appended claims.

It is to be understood that both the foregoing general description and the following detailed description are exemplary and explanatory only and are not restrictive of the present disclosure, as claimed.

The accompanying drawings, which are incorporated in and constitute a part of this specification, illustrate one (several) embodiment(s) of the present disclosure and together with the description, serve to explain the principles of the disclosure.

BRIEF DESCRIPTION OF THE DRAWINGS

FIG. 3D depicts a photomicrographic image of representative mitochondrial staining of oocytes obtained from animals in each of the acute dietary treatment groups. FIG. 3E depicts a photomicrographic image of representative tubulin (spindle apparatus, green) and DNA (blue) staining of oocytes obtained from animals in each of the acute dietary treatment groups.

FIG. 4A-4D are graphs of serum fatty acid profiles over multiple generations (N=4, 5, 5, 5, 4, 15 for F1 HCO, F1 SOY, F2 SOY, F1 DHA, F2 DHA and F5 DHA groups, respectively). FIGS. 4E-4H are graphs of growth data.

DESCRIPTION

Figure 1A:
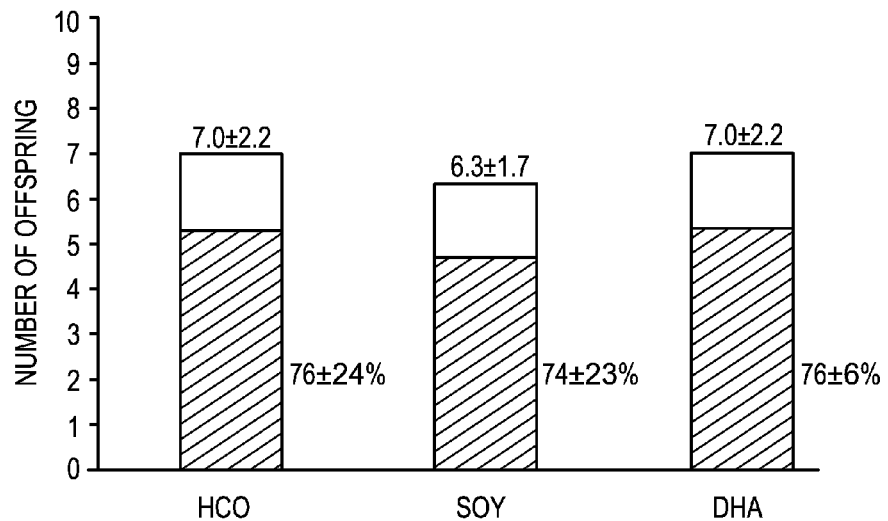
FIGS. 1A and 1B are graphs of the reproductive and fertility outcomes in long-term diet studies at normal murine maternal reproductive age (3-6 months), as described in Example 2.

As used herein, "fertility" refers to the capability of a female to produce an egg which can be successfully fertilized, implanted, and can develop into a healthy fetus which survives birth. Therefore, fertility includes the quality of the oocyte or ovum, both of which can be considered unfertilized egg cells, (e.g. a lack of chromosomal abnormalities), later division and development of the egg or oocyte into a fetus, as well as the health and function of any aspect of the female's reproductive system which contributes to normal, healthy development and delivery of offspring. Examples of chromosomal abnormalities that can be treated, abrogated or ameliorated by the methods described herein, include 22q11.2 deletion syndrome, Angelman syndrome, Canavan disease, Coeliac disease, Charcot-Marie-Tooth disease, Color blindness, Cri du chat, Cystic fibrosis, Down Syndrome, Duchenne muscular dystrophy, Haemochromatosis, Haemophilia, Klinefelter's syndrome, Neurofibromatosis, Phenylketonuria, Polycystic kidney disease, Prader-Willi syndrome, Sickle-cell disease, Tay-Sachs disease, and Turner syndrome. In at least one embodiment, the chromosomal abnormality is Down Syndrome.

A subject can be one who desires to become pregnant and is concerned about birth defects and/or infant or fetus mortality. A subject can be a one who desires to become pregnant and is concerned about birth defects and/or infant or fetus mortality due to a family history of such pregnancy complications. A subject can be a subject who desires to become pregnant and is more likely to experience birth defects and/or infant or fetus mortality due to the subject's age, e.g. the subject is 30 years old or older, e.g. 35 years old, or 40 years old, or older. A subject can be a subject who desires to become pregnant and is more likely to experience birth defects and/or infant or fetus mortality due to a family history of such complications. A subject can be a subject who desires to become pregnant and is more likely to experience birth defects and/or infant or fetus mortality due to a personal history of such complications.

A subject can be a subject who desires to become pregnant and has had difficulty conceiving. A subject can be a subject who desires to become pregnant, has had difficulty conceiving, and is recommended to undergo fertility treatments or artificial conception methods through a pre-defined protocol (e.g. in vitro fertilization).

For example, in some embodiments, the methods described herein relate to prolonging or enhancing fertility in a subject. In some embodiments, the subject can be a female mammal. In some embodiments, the subject can be a female human. In some embodiments, the subject is a female human of at least 18 years of age, e.g. 18 years old, 20 years old, 25 years old, 30 years old, 35 years old, 40 years old, any age in between, or older. In some embodiments, the subject is a female human of at least 30 years of age. In some embodiments, the subject is a female human of at least 35 years of age. In some embodiments, the subject is a female human of at least 40 years of age.

Measures of fertility can include, for example, the rate of birth defects, the rate of chromosomal abnormalities, the rate of Down Syndrome, the egg quality, the mitochondrial dynamics of the egg, the structure of the spindle apparatus of the egg, and/or the survival of the offspring both in utero and following delivery.

In some embodiments of the methods described herein, consumption of a diet rich in omega-3 fatty acids sufficient to achieve a serum ratio of omega-3 fatty acids to omega-6 fatty acids of at least 1:8 increases oocyte or ovum quality. The methods described herein can be used in both natural and assisted reproduction such as in vitro fertilization. In some embodiments, the methods described herein relate to enhancing or prolonging fertility at advanced maternal age. In some embodiments, the serum ratio of omega-3 fatty acids to omega-6 fatty acids can be from about 1:8 to 8:1. In some embodiments, the serum ratio of omega-3 fatty acids to omega-6 fatty acids can be at least 2:1, e.g. 2:1 or greater, 1:1 or greater, or 2:1 or greater. In some embodiments, the serum ratio of omega-3 fatty acids to omega-6 fatty acids can be at least 1:1, e.g. 1:1 or greater, 2:1 or greater, or 3:1 or greater. In some embodiments, the serum ratio of omega-3 fatty acids to omega-6 fatty acids is 2:1. In some embodiments, the serum ratio of omega-3 fatty acids to omega-6 fatty acids is 1:0.5. In some embodiments, the serum ratio of omega-3 fatty acids to omega-6 fatty acids is 1:2. In some embodiments, the serum ratio of omega-3 fatty acids to omega-6 fatty acids is 7:1. In some embodiments, the serum ratio of omega-3 fatty acids to omega-6 fatty acids is 8:1.

The methods described herein comprise administration and/or use of a fatty acid composition. In some embodiments, the fatty acid composition disclosed herein comprises a pharmacological or medical food fatty acid composition. In some embodiments, the fatty acid composition disclosed herein comprises a nutritional, dietary, or food fatty acid supplement. In other embodiments, the fatty acid composition disclosed herein comprises a nutritional supplement, a dietary supplement, a food supplement, a pharmaceutical grade supplement, and a medical food. In some embodiments, the fatty acid composition disclosed herein can be administered orally or intravenously. In other embodiments, the fatty acid composition disclosed herein can be administered enterally or parenterally. Enteral administration may be chosen, for example, from oral, gastric, and rectal. Parenteral administration may be chosen, for example, from infusion, injection, and implantation.

As used herein, the term "fatty acid" includes fatty acids such as unsaturated (e.g., monounsaturated, polyunsaturated) or saturated fatty acids, as well as pharmaceutically-acceptable esters, free acids, mono-, di- and triglycerides, derivatives, conjugates, precursors, salts, and mixtures thereof. In some embodiments, the fatty acids, such as omega-3 fatty acids, are in a form chosen from ethyl ester and triglyceride. In other embodiments, the fatty acids are in free acid form.

As used herein, the term "omega-3 fatty acids" includes natural and synthetic omega-3 fatty acids, as well as pharmaceutically acceptable esters, free acids, triglycerides, derivatives, conjugates (see, e.g., Zaloga et al., U.S. Patent Application Publication No. 2004/0254357, and Horrobin et al., U.S. Pat. No. 6,245,811, each hereby incorporated by reference), precursors, salts, and mixtures thereof. Omega-3 fatty acids can include, but are not limited to, Hexadecatrienoic acid (HTA); α-Linolenic acid (ALA); Stearidonic acid (SDA); Eicosatrienoic acid (ETE); Eicosatetraenoic acid (ETA); Eicosapentaenoic acid (EPA); Heneicosapentaenoic acid (HPA); Docosapentaenoic acid (DPA); Clupanodonic acid; Docosahexaenoic acid (DHA); Tetracosapentaenoic acid; and Tetracosahexaenoic acid (Nisinic acid).

The fatty acid(s) according to the present disclosure may be derived from animal oils and/or non-animal oils. In some embodiments of the present disclosure, the fatty acid(s) are derived from at least one oil chosen from marine oil, algae oil, plant-based oil, and microbial oil. Marine oils include, for example, fish oil, such as tuna fish oil, hill oil, and lipid composition derived from fish. Plant-based oils include, for example, flaxseed oil, canola oil, mustard seed oil, and soybean oil. Microbial oils include, for example, products by Martek. In at least one embodiment of the present disclosure, the fatty acid(s) are derived from a marine oil, such as a fish oil. In at least one embodiment, the marine oil is a purified fish oil.

In some embodiments of the present disclosure, the fatty acids, such as omega-3 fatty acids, are esterified, such as alkyl esters and further for example, ethyl esters. In other embodiments, the fatty acids are chosen from mono-, di-, and triglycerides.

In some embodiments, the fatty acid(s) are obtained by a transesterification of the body oil of a fat fish species coming from, for example, anchovy or tuna oil, and subsequent physio-chemical purification processes, including urea fractionation followed by molecular distillation. In some embodiments, the crude fatty acid(s) may also be subjected to a stripping process for decreasing the amount of environmental pollutants and/or cholesterol before the transesterification.

In another embodiment, the fatty acid(s) are obtained by using supercritical $CO_2$ extraction or chromatography techniques, for example to up-concentrate primary EPA and DHA from fish oil concentrates.

The fatty acid(s) of the present disclosure comprise omega-3 fatty acids, such as EPA, DHA, or combination thereof. Further for example, in some embodiments, the fatty acid(s) comprise EPA and DHA in a form chosen from ethyl ester and triglyceride. In other embodiments, the fatty acid(s) comprise EPA and DHA in free acid form. In at least one embodiment, the fatty acid composition comprises DHA in triglyceride form.

The fatty acid(s) of the present disclosure may further comprise at least one fatty acid other than DHA in a form chosen from ethyl ester, free fatty acid, and triglyceride. Examples of such fatty acids include, but are not limited to, omega-3 fatty acids other than DHA and omega-6 fatty acids. For example, in some embodiments of the present disclosure, the fatty acid composition comprises at least one fatty acid other than DHA chosen from EPA, arachidonic acid, α-linolenic acid, heneicosapentaenoic acid, docosapentaenoic acid, eicosatetraenoic acid, and octadecatetraenoic acid. Examples of further omega-3 fatty acids and mixtures thereof encompassed by the present disclosure include the omega-3 fatty acids as defined in the European Pharmacopoeia Omega-3 Triglycerides, the European Pharmacopoeia Omega-3 acid Ethyl Esters 60, or the Fish oil rich in omega-3 acids monograph. In some embodiments, the at least one fatty acid other than EPA and DHA is in a form chosen from ethyl ester and triglyceride. In other embodiments, the at least one fatty acid other than EPA and DHA is in free acid form.

Commercial examples of omega-3 fatty acids suitable for the present disclosure comprise different fatty acid mixtures (e.g., that can be in the form of triglycerides (TG), ethyl esters (EE), free fatty acid form (FA) and/or as phospholipids) including, but not limited to: Incromega™ omega-3 marine oil concentrates such as Incromega™ E1070, Incromega™ TG7010 SR, Incromega™ E7010 SR, Incromega™ TG6015, Incromega™ EPA500TG SR, Incromega™ E400200 SR, Incromega™ E4010, Incromega™ DHA700TG SR, Incromega™ DHA700E SR, Incromega™ DHA500TG SR, Incromega™ TG3322 SR, Incromega™ E3322 SR, Incromega™ TG3322, Incromega™ E3322, Incromega™ Trio TG/EE (Croda International PLC, Yorkshire, England); EPAX6000FA, EPAX5000TG, EPAX4510TG, EPAX2050TG, EPAX7010EE, EPAX5500EE, EPAX5500TG, EPAX5000EE, EPAX5000TG, EPAX6000EE, EPAX6000TG, EPAX6000FA, EPAX6500EE, EPAX6500TG, EPAX4510TG, EPAX1050TG, EPAX2050TG, EPAX 7010TG, EPAX7010EE, EPAX6015TG/EE, EPAX4020TG, and EPAX4020EE (EPAX is a wholly-owned subsidiary of Norwegian company Austevoll Seafood ASA); MEG-3® EPA/DHA fish oil concentrates (Ocean Nutrition Canada); DHA FNO "Functional Nutritional Oil" and DHA CL "Clear Liquid" (Lonza); Superba™ Krill Oil (Aker); omega-3 products comprising DHA produced by Martek; Neptune hill oil (Neptune); cod-liver oil products and anti-reflux fish oil concentrate (TG) produced by Møllers; Lysi Omega-3 Fish oil; Seven Seas Triomega® Cod Liver Oil Blend (Seven Seas); and Fri Flyt Omega-3 (Vesterålens).

In some embodiments, the fatty acid composition comprises a weight ratio of omega-3 fatty acids to omega-6 fatty acids of about 10:1 or greater. In other embodiments, the fatty acid composition comprises a weight ratio of omega-3 fatty acids to omega-6 fatty acids is about 20:1, 21:1, 22:1, 23:1, 24:1, 25:1, or greater. In at least one embodiment, the fatty acid composition comprises from about 750 mg to about 900 mg total omega-3 fatty acids. In some embodiments, the fatty acid composition comprises at least 70%, at least 75%, at least 80%, or at least 90% omega-3 fatty acids, by weight of the total fatty acids in the composition.

In some embodiments, the fatty acid composition comprises DHA and further comprises EPA in a form chosen from ethyl ester, free fatty acid, and triglyceride. In some embodiments, the fatty acid composition comprises DHA and further comprises arachidonic acid in a form chosen from ethyl ester, free fatty acid, and triglyceride.

In at least one embodiment, the fatty acid composition comprises DHA and further comprises EPA in a form chosen from ethyl ester, free fatty acid, and triglyceride, wherein DHA is present in an amount greater than EPA; and arachidonic acid in a form chosen from ethyl ester, free fatty acid, and triglyceride, wherein the weight ratio of omega-3 fatty acids to omega-6 fatty acids is 10:1 or greater. Such an embodiment may further comprise vitamin D.

In some embodiments, the fatty acid composition comprises DHA and EPA present in an amount chosen from about 35% to about 90% by weight of the total fatty acids in the composition, from about 40% to about 85% by weight of the total fatty acids in the composition, from about 40% to about 80% by weight of the total fatty acids in the composition, and from about 50% to about 80% by weight of the total fatty acids in the composition. In at least one embodiment, the fatty acid composition comprises EPA and DHA in ethyl ester form and comprise at least about 84% by weight of the total fatty acids in the composition.

In some embodiments of the fatty acid compositions of the present disclosure, the weight ratio of EPA:DHA ranges from about 1:10 to about 10:1, from about 1:8 to about 8:1, from about 1:6 to about 6:1, from about 1:5 to about 5:1, from about 1:4 to about 4:1, from about 1:3 to about 3:1, or from about 1:2 to about 2:1. In at least one embodiment, the EPA:DHA weight ratio ranges from 1:2 to 2:1. In other embodiments, the weight ratio of DHA:EPA ranges from about 500:1 to 1:500 such as 500:1, 100:1, 50:1, 20:1, 15:1, 10:1, 9:1, 8:1, 7:1, 6:1, 5:1, 4:1, 3:1, or 2:1, to about 1:1.

In at least one embodiment of the fatty acid compositions disclosed herein, the concentration by weight of DHA is greater than the concentration by weight of EPA relative to the total fatty acids in the fatty acid composition. In such embodiments, DHA is present in an amount greater than EPA.

In some embodiments of the fatty acid composition, DHA is present in an amount ranging from about 500 mg to about 750 mg, and EPA is present in an amount ranging from about 80 mg to about 250 mg. In such embodiments, DHA and EPA may be present at a DHA:EPA weight ratio chosen from 70:10, 500:200, and 600-750:150-250. In at least one embodiment, the fatty acid composition comprises from about 650 mg to about 750 mg DHA and from about 80 mg to about 130 mg EPA. The fatty acid composition comprises from about 750 mg to about 900 mg total omega-3 fatty acids in at least one embodiment.

In another embodiment, the fatty acid composition comprises pure DHA, such as greater than 90% DHA, such as greater than 95% DHA, in free fatty acid, triglyceride, or ethyl ester form, relative to the total fatty acids in the composition.

In yet another embodiment, the fatty acid composition comprises pure EPA, such as greater than 90% EPA, such as greater than 95% EPA, in free fatty acid, triglyceride, or ethyl ester form, relative to the total fatty acids in the composition.

In still another embodiment, DHA is the predominant fatty acid in the fatty acid composition disclosed herein.

In at least one embodiment, the fatty acid composition comprises a weight ratio of EPA:DHA of 1.2:1 (from about 430 to about 495 mg/g EPA ethyl ester and from about 347 to about 403 mg/g DHA ethyl ester) and a total amount of omega-3 fatty acid ethyl esters of at least about 800 mg/g omega-3 fatty acids.

The fatty acid compositions presently disclosed may further comprise at least one antioxidant. Examples of antioxidants suitable for the present disclosure include, but are not limited to, α-tocopherol (vitamin E), calcium disodium EDTA, alpha tocoferyl acetates, butylhydroxytoluenes (BHT), and butylhydroxyanisoles (BHA). Other examples of antioxidants include ascorbic acid and pharmaceutically acceptable salts thereof such as sodium ascorbate, pharmaceutically acceptable esters of ascorbic acid including fatty acid ester conjugates, propyl gallate, citric acid and pharmaceutically acceptable salts thereof, malic acid and pharmaceutically acceptable salts thereof, and sulfite salts such as sodium sulfite and mixtures thereof.

In some embodiments, the fatty acid composition disclosed herein further comprises Vitamin D. Vitamin D, or calciferol, is the general name for a collection of steroid-like substances including vitamin $D_2$, ergocalciferol, and vitamin $D_3$, cholecalciferol. The latter is the naturally occurring form used for low dose supplementation.

The term "vitamin D" used herein, means vitamin $D_3$. Vitamin $D_3$ is a secosteroid. The IUPAC name is (3β,5Z,7E)-9,10-secocholesta-5,7,10(19)-trien-3-ol. Another name is activated 7-dehydrocholesterol. The chemical structure of vitamin $D_3$ is as follows:

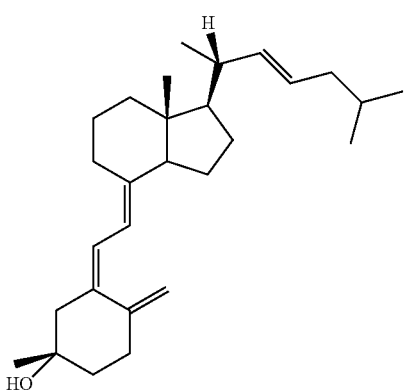 [SMILES: C=C1CC[C@](C)(O)C/C1=C/C=C1\CCC[C@@]2(C)C1CC[C@@H]2[C@H](C)/C=C/CC(C)C]

Vitamin $D_3$ is metabolised by the liver to $25(OH)D_3$ (also known as 25 hydroxycholecalciferol, calcifediol, or calcidiol), which is then converted by the kidneys to $1,25(OH)_2D_3$ (also known as 1,25 dihydroxycholecalciferol, calcitriol, or active vitamin D hormone). $25(OH)D_3$, the major circulating form, has some metabolic activity, but $1,25(OH)_2D_3$ is the most metabolically active.

The chemical structure of $25(OH)D_3$ is as follows:

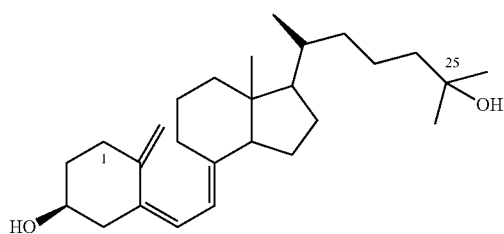

The chemical structure of $1,25(OH)_2D_3$ is as follows:

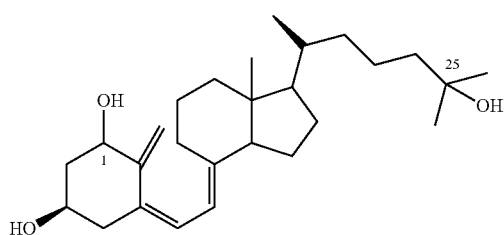

The daily dose of Vitamin $D_3$ will be from 400-4000 International Units (IU) optionally divided into 2-4 capsules or tablets or any other formulation of the omega-3 fatty acid composition. For example, in at least one embodiment, the daily dose of Vitamin $D_3$ ranges from about 1000 to about 4000 IU or from about 2000 to about 4000 IU.

The compositions presently disclosed may further comprise at least one other vitamin other than vitamin D. Examples of other vitamins suitable for the present disclosure include, but are not limited to, Zinc and Magnesium.

In some embodiments, the fatty acid composition comprises omega-3-acid ethyl esters, e.g. LOVAZA™ (GlaxoSmithKline; Brentford, United Kingdom).

A refined or highly-refined fish oil product can be administered to the subject according to the methods described herein. A non-limiting example of a highly refined fish oil product is OMEGAVEN™ (Fresenius Kabi; Bad Homburg, Germany) and which is not administered orally, but intravenously. In some embodiments, a refined or highly-refined fish oil product can be administered intravenously in order to treat a subject according to the methods described herein in a time of about 3 months or less, e.g. 3 months or less, 2 months or less, one month or less, 3 weeks or less, 2 weeks or less, or 1 week or less. In some embodiments, a refined or highly-refined fish oil product can be administered intravenously in order to treat a subject according to the methods described herein in a short time, e.g. less than a week.

In some embodiments, the fatty acid composition comprises a dietary formulation in the form of a food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. In some embodiment, the dietary formulation comprises 0.15% to 0.30% by calories of arachidonic acid, or 0.15% to 0.6% by calories of archidonic acid. In some embodiment, the $C_{20}$ or longer omega-3 fatty acid consists of eicosapentaenoic acid (EPA), or docosahexaenoic acid (DHA), or eicosatetraenoic acid, or 5-docosapentaenoic acid, or combinations thereof; and comprises about 0% by calories of omega-6 fatty acids other than arachidonic acid, about 0% by calories of linoleic acid, and about 0% by calories of alpha-linolenic acid. For example, the ratio of $C_{20}$ or longer omega-3 fatty acid to arachidonic acid is from about 10:1 to about 40:1. For example, the ratio is about 10:1, about 20:1, about 30:1, or about 40:1. In some embodiments, the arachidonic acid is provided as dihomo-gamma-linolenic acid or gamma-linolenic acid which is converted in vivo to arachidonic acid, wherein the dihomo-gamma-linolenic acid or gamma-linolenic acid is provided in amounts of 0.45% to 6.0% by calories. In some embodiments, the $C_{20}$ or longer omega-3 fatty acid is selected from the group consisting of eicosapentaenoic acid (EPA), docosahexaenoic acid (DHA), an octadecatetraenoic acid, an eicosatetraenoic acid, α-linolenic acid (ALA) and mixtures thereof. Such compositions and related compositions which can be used in the methods described herein are described in U.S. Patent Publication No. 2010/0256235; which is incorporated by reference herein in its entirety.

In some embodiments, the subject receives a dose of the composition comprising an omega-3 fatty acid such that the total fatty acid intake of the subject comprises a ratio of total omega-3 fatty acids to omega-6 fatty acids of from about 10:1 to 40:1. In some embodiments, the subject receives a dose of the composition comprising an omega-3 fatty acid such that the total fatty acid intake of the subject comprises a ratio of total omega-3 fatty acids to omega-6 fatty acids of 20:1 or greater, e.g. 20:1, 21:1, 22:1, 23:1, 24:1 25:1, or greater.

In some embodiments, the subject is treated according to the method described herein for at least 1 day, at least 1 week, at least 1 month, at least 2 months, or longer. In some embodiments, the subject is administered a composition comprising an omega-3 fatty acid for at least 1 day, at least 1 week, at least 1 month, at least 2 months, or longer before being treated with a protocol, procedure or treatment to enhance fertility and/or impregnate the subject. In some embodiments, the subject is administered the composition comprising an omega-3 fatty acid for at least 1 week prior to the protocol, treatment or procedure. In some embodiments, the subject is administered the composition comprising an omega-3 fatty acid for at least 1 month prior to the protocol, treatment or procedure. In some embodiments, the subject is administered the composition comprising an omega-3 fatty acid for at least 2 months prior to the protocol, treatment or procedure. In some embodiments, the subject is administered the composition comprising an omega-3 fatty acid for at least 3 months prior to the protocol, treatment or procedure.

In some embodiments, when the fatty acid composition is a nutritional, dietary, or food fatty acid supplement, the daily dosage per day of the total fatty acids in the supplement may range, for example, from about 1 to about 8 grams, such as from about 2 to about 4 grams. In other embodiments, the daily dosage per day of the total fatty acids in the supplement may range, for example, from about 2 to about 8 grams.

In yet other embodiments, when the fatty acid composition is a pharmaceutical or medical food fatty acid composition, the daily dosage per day of the total fatty acids in the pharmaceutical or the medical food may range from about 2 g to about 8 g.

In some embodiments of the methods described herein, an in vitro fertilization (IVF) protocol is enhanced. In some embodiments, the IVF protocol comprises the steps of 1) stimulating multiple follicles to cause multiple unfertilized egg cells to develop, 2) retrieving the unfertilized egg cells from the female, 3) fertilizing the egg cells in vitro, and 4) transferring the fertilized embryo to the uterus. Those skilled in the art will recognize that improving oocyte or ovum quality (otherwise known as egg cell quality) can be readily incorporated into any fertilization method or fertilization protocol because higher quality oocyte or ovum will result in higher success rates of the method or protocol being employed. In some embodiments of the methods described herein, the oocyte, ovum or fertilized egg is cryopreserved.

Further, the methods described herein can result in delaying the onset or progression of menopause, i.e. fertility can be maintained and/or a natural decrease in fertility can be reduced. Any of the embodiments of the methods described herein can relate to methods of delaying the onset or progression of menopause. It is contemplated that a subject can be treated according to the methods described herein when the subject desires to have children (e.g. by IVF), but not immediately, i.e. the subject can be treated or administered according to any of the methods described herein while a subject is reproductively mature (e.g. after menstruation begins) and continue until the subject enters menopause and/or no longer desires to maintain, enhance, and/or improve fertility. In some embodiments, a subject can be treated according to any of the methods described herein when the subject reaches an age of decreasing fertility and/or an age when the onset of menopause may reasonably occur, e.g. at least 25 years of age, at least 30 years of age, at least 35 years or age, or older. In some embodiments, the subject can be at least 25 years of age when treatment according to any of the methods described herein is begun. In some embodiments, the subject can be at least 30 years of age when treatment according to any of the methods described herein is begun. In some embodiments, the subject can be at least 35 years of age when treatment according to any of the methods described herein is begun. In some embodiments, the subject can be administered an oral composition as described herein.

Other embodiments of the present disclosure will be apparent to those skilled in the art from consideration of the specification and practice of the disclosure herein. It is intended that the specification and examples be considered as exemplary only, with a true scope and spirit of the disclosure indicated by the following claims.

Some embodiments of the technology described herein can be defined according to any of the following numbered paragraphs:

1. A method for enhancing, improving, or increasing a female human's likelihood of becoming pregnant comprising:
    administering to the human a nutritional, dietary, or food fatty acid supplement comprising:
    at least 30% docosahexaenoic acid (DHA), by weight of the total fatty acids in the supplement in a form chosen from ethyl ester, free fatty acid, and triglyceride.

2. The method according to paragraph 1, wherein the supplement further comprises eicosapentaenoic acid (EPA) in a form chosen from ethyl ester, free fatty acid, and triglyceride.

3. The method according to paragraph 1 or 2, wherein the supplement further comprises arachidonic acid in a form chosen from ethyl ester, free fatty acid, and triglyceride.

4. The method of according to paragraph 1, wherein the DHA is in the form of triglyceride.

5. The method according to paragraph 1, wherein the supplement further comprises vitamin D.

6. The method according to paragraph 5, wherein the vitamin D is present in an amount ranging from about 400 to about 4000 International Units (IU), from about 1000 to about 4000 IU, or from about 2000 to about 4000 IU.

7. The method according to paragraph 5, wherein the supplement further comprises at least one vitamin other than vitamin D.

8. The method according to paragraph 2, wherein the weight ratio of the DHA to the EPA ranges from about 500:1, 100:1, 50:1, 20:1, 15:1, 10:1, 9:1, 8:1, 7:1, 6:1, 5:1, 4:1, 3:1, 2:1, to 1:1.

9. The method according to paragraph 3, wherein the weight ratio of the omega-3 fatty acids to the omega-6 fatty acids is about 10:1 or greater.

10. The method according to paragraph 9, wherein the weight ratio of the omega-3 fatty acids to omega-6 fatty acids is about 20:1, 21:1, 22:1, 23:1, 24:1, 25:1 or greater.

11. The method according to paragraph 2, wherein DHA is present in an amount greater than EPA.

12. The method according to paragraph 11, wherein DHA is present in an amount ranging from about 500 mg to about 750 mg, and EPA is present in an amount ranging from about 80 mg to about 250 mg.

13. The method according to paragraph 12, wherein DHA: EPA are present in a weight ratio chosen from about 70:10, 500:200, and 600-750:150-250.

14. The method according to paragraph 2, wherein the supplement comprises from about 650 mg to about 750 mg DHA and from about 80 mg to about 130 mg EPA.

15. The method according to paragraph 1, wherein the supplement comprises from about 750 mg to about 900 mg total omega-3 fatty acids.

16. The method according to paragraph 1, wherein the supplement further comprises at least one antioxidant.

17. The method according to paragraph 16, wherein the at least one antioxidant is chosen from α-tocopherol (vitamin E), calcium disodium EDTA, alpha tocoferyl acetates, butylhydroxytoluenes (BHT), butylhydroxyanisoles (BHA), ascorbic acid and pharmaceutically acceptable salts and esters thereof, propyl gallate, citric acid and pharmaceutically acceptable salts thereof, malic acid and pharmaceutically acceptable salts thereof, and sulfite salts and mixtures thereof.

18. The method according to paragraph 17, wherein the at least one antioxidant comprises BHA.

19. The method according to paragraph 1, 2 or 3, wherein the fatty acid is derived from at least one oil chosen from marine oil, algae oil, plant-based oil, and microbial oil.

20. The method according to paragraph 19, wherein the oil is tuna fish oil.

21. The method according to paragraph 1, wherein the total omega-3 fatty acids are at least 70%, at least 75%, at least 80%, or at least 90%, by weight of the total fatty acids in the supplement.

22. The method according to paragraph 2, wherein DHA and EPA are present in an amount chosen from about 35% to about 90% by weight of the total fatty acids in the supplement, from about 40% to about 85% by weight of the total fatty acids in the supplement, from about 40% to about 80% by weight of the total fatty acids in the supplement, and from about 50% to about 80% by weight of the total fatty acids in the supplement.

23. The method according to paragraph 1, wherein the supplement comprises at least one other fatty acid other than DHA in a form chosen from ethyl ester, free fatty acid, and triglyceride.

24. The method according to paragraph 1, wherein the supplement comprises at least one omega-3 fatty acid other than DHA chosen from those defined in the European Pharmacopoeia Omega-3 Triglycerides and the European Pharmacopoeia Omega-3 acid Ethyl Esters 60.

25. The method according to paragraph 2, wherein the supplement further comprises: eicosapentaenoic acid (EPA) in a form chosen from ethyl ester, free fatty acid, and triglyceride, wherein DHA is present in an amount greater than EPA; and arachidonic acid in a form chosen from ethyl ester, free fatty acid, and triglyceride, wherein the weight ratio of omega-3 fatty acids to omega-6 fatty acids is 10:1 or greater.

26. The method according to paragraph 25, wherein the supplement further comprises vitamin D.

27. The method according to paragraph 1, wherein the daily dosage per day of the total fatty acids in the supplement ranges from 1 to 8 grams.

28. The method according to paragraph 27, wherein the daily dosage per day of the total fatty acids in the supplement ranges from 2 to 4 grams.

29. The method according to paragraph 1, wherein DHA is present in an amount of at least 90% by weight of the total fatty acids in the supplement.

30. The method according to paragraph 29, wherein the DHA is present in an amount of at least 95% by weight of the total fatty acids in the supplement.

31. A method of maintaining or improving oocyte and/or ovum quality in a human in need thereof comprising:
administering to the human a nutritional, dietary, or food fatty acid supplement comprising:
at least 30% docosahexaenoic acid (DHA), by weight of the total fatty acids in the supplement in a form chosen from ethyl ester, free fatty acid, and triglyceride.

32. The method according to paragraph 31, wherein the supplement further comprises eicosapentaenoic acid (EPA) in a form chosen from ethyl ester, free fatty acid, and triglyceride.

33. The method according to paragraph 31 or 32, wherein the supplement further comprises arachidonic acid in a form chosen from ethyl ester, free fatty acid, and triglyceride.

34. The method according to paragraph 31, wherein the DHA is in the form of triglyceride.

35. The method according to paragraph 31, wherein the supplement further comprises vitamin D.

36. The method according to paragraph 35, wherein the vitamin D is present in an amount ranging from about 400 to about 4000 International Units (IU), from about 1000 to about 4000 IU, or from about 2000 to about 4000 IU.

37. The method according to paragraph 35, wherein the supplement further comprises at least one vitamin other than vitamin D.

38. The method according to paragraph 32, wherein the weight ratio of the DHA to the EPA ranges from about 500:1, 100:1, 50:1, 20:1, 15:1, 10:1, 9:1, 8:1, 7:1, 6:1, 5:1, 4:1, 3:1, 2:1, to 1:1.

39. The method according to paragraph 33, wherein the weight ratio of the omega-3 fatty acids to the omega-6 fatty acids is about 10:1 or greater.

40. The method according to paragraph 39, wherein the weight ratio of the omega-3 fatty acids to omega-6 fatty acids is about 20:1, 21:1, 22:1, 23:1, 24:1, 25:1 or greater.

41. The method according to paragraph 32, wherein DHA is present in an amount greater than EPA.

42. The method according to paragraph 41, wherein DHA is present in an amount ranging from about 500 mg to about 750 mg, and EPA is present in an amount ranging from about 80 mg to about 250 mg.

43. The method according to paragraph 41, wherein DHA: EPA are present in a weight ratio chosen from about 70:10, about 500:200, and about 600-750:150-250.

44. The method according to paragraph 41, wherein the supplement comprises from about 80 mg/g to about 130 mg/g EPA ethyl ester, free fatty acid, or triglyceride and from about 650 mg/g to about 750 mg/g DHA ethyl ester, free fatty acid, or triglyceride.

45. The method according to paragraph 31, wherein the supplement comprises from about 750 mg/g to about 900 mg/g total omega-3 fatty acids.

46. The method according to paragraph 31, wherein the supplement further comprises at least one antioxidant.

47. The method according to paragraph 46, wherein the at least one antioxidant is chosen from α-tocopherol (vitamin E), calcium disodium EDTA, alpha tocoferyl acetates, butylhydroxytoluenes (BHT), butylhydroxyanisoles (BHA), ascorbic acid and pharmaceutically acceptable salts and esters thereof, propyl gallate, citric acid and pharmaceutically acceptable salts thereof, malic acid and pharmaceutically acceptable salts thereof, and sulfite salts and mixtures thereof.

48. The method according to paragraph 47, wherein the at least one antioxidant comprises BHA.

49. The method according to paragraph 31, 32, or 33, wherein the fatty acid is derived from at least one oil chosen from marine oil, algae oil, plant-based oil, and microbial oil.

50. The method according to paragraph 49, wherein the oil is tuna fish oil.

51. The method according to paragraph 31, wherein the total omega-3 fatty acids are at least 70%, at least 75%, at least 80%, or at least 90%, by weight of the total fatty acids in the supplement.

52. The method according to paragraph 32, wherein DHA and EPA are present in an amount chosen from about 35% to about 90% by weight of the total fatty acids in the supplement, from about 40% to about 85% by weight of the total fatty acids in the supplement, from about 40% to about 80% by weight of the total fatty acids in the supplement, and from about 50% to about 80% by weight of the total fatty acids in the supplement.

53. The method according to paragraph 31, wherein the supplement comprises at least one other fatty acid other than DHA in a form chosen from ethyl ester, free fatty acid, and triglyceride.

54. The method according to paragraph 31, wherein the supplement comprises at least one omega-3 fatty acid chosen from those defined in the European Pharmacopoeia Omega-3 Triglycerides and the European Pharmacopoeia Omega-3 acid Ethyl Esters 60.

55. The method according to paragraph 31, wherein the supplement further comprises: eicosapentaenoic acid (EPA) in a form chosen from ethyl ester, free fatty acid, and triglyceride, wherein DHA is present in an amount greater than EPA; and arachidonic acid in a form chosen from ethyl ester, free fatty acid, and triglyceride, wherein the weight ratio of omega-3 fatty acids to omega-6 fatty acids is 10:1 or greater.

56. The method according to paragraph 55, wherein the supplement further comprises vitamin D.

57. The method according to paragraph 31, wherein the daily dosage per day of the total fatty acids in the supplement ranges from 1 to 8 grams.

58. The method according to paragraph 57, wherein the daily dosage per day of the total fatty acids in the supplement ranges from 2 to 4 grams.

59. The method according to paragraph 31, wherein DHA is present in an amount of at least 90% by weight of the total fatty acids in the supplement.

60. The method according to paragraph 59, wherein the DHA is present in an amount of at least 95% by weight of the total fatty acids in the supplement.

61. The method according to paragraph 31, wherein the oocyte and/or ovum quality is maintained or improved by decreasing the likelihood of abnormalities in at least one of spindle integrity and mitochondrial dynamics in the oocyte and/or ovum.

62. The method according to paragraph 31, wherein the oocyte and/or ovum quality is maintained or improved by decreasing the likelihood of at least one chromosomal abnormality in the oocyte and/or ovum.

63. The method according to paragraph 62, wherein the at least one chromosomal abnormality is chosen from 22q11.2 deletion syndrome, Angelman syndrome, Canavan disease, Coeliac disease, Charcot-Marie-Tooth disease, color blindness, Cri du chat, Cystic fibrosis, Down Syndrome, Duchenne muscular dystrophy, Haemochromatosis, Haemophilia, Klinefelter's syndrome, Neurofibromatosis, Phenylketonuria, Polycystic kidney disease, Prader-Willi syndrome, Sickle-cell disease, Tay-Sachs disease, and Turner syndrome.

64. The method according to paragraph 63, wherein the at least one chromosomal abnormality is Down Syndrome.

65. The method according to paragraph 31, wherein the supplement is enterally or parenterally administered.

66. The method of paragraph 65, wherein the supplement is enterally administrated and the enteral administration is chosen from oral, gastric, and rectal.

67. The method of paragraph 65, wherein the supplement is parenterally administered and the parenteral administration is chosen from infusion, injection, and implantation.

68. The method according to paragraph 31, wherein the human is at least 25 years of age, at least 30 years of age, or at least 35 years of age.

69. The method according to paragraph 31, wherein the human is undergoing infertility treatment.

70. A method of treating infertility in a female human in need thereof comprising:
administering to the human a pharmaceutical or medical food fatty acid composition comprising:
at least 80% docosahexaenoic acid (DHA) in a form chosen from ethyl ester, free fatty acid, and triglyceride, and eicosapentaenoic acid (EPA) in a form chosen from ethyl ester, free fatty acid, and triglyceride, by weight of the total fatty acids in the composition.

71. The method according to paragraph 70, wherein the daily dosage per day of the total fatty acids in the pharmaceutical or the medical food ranges from about 2 g to about 8 g.

72. A method of enhancing, improving, or increasing a female human's likelihood of becoming pregnant comprising:
administering to the human a nutritional, dietary, or food fatty acid supplement comprising:
at least 80% docosahexaenoic acid (DHA) in a form chosen from ethyl ester, free fatty acid, and triglyceride, and eicosapentaenoic acid (EPA) in a form chosen from ethyl ester, free fatty acid, and triglyceride, by weight of the total fatty acids in the supplement.

73. The method according to paragraph 72, wherein the daily dose per day of the total fatty acids ranges from about 2 g to about 8 g.

74. The method according to paragraph 70 or 72, wherein the EPA:DHA ratio ranges from 1:2 to 2:1.

75. The method according to paragraph 70 or 72, wherein the EPA and DHA are in ethyl ester form and comprise at least about 84% by weight of the total fatty acids in the composition or supplement.

76. The method according to paragraph 70 or 72, wherein the composition or supplement comprises about 430-495 mg/g EPA ethyl ester, about 347-403 mg/g DHA ethyl ester, and at least about 800 mg/g omega-3 fatty acids.

77. A method of enhancing and/or prolonging fertility and/or reproductive function in a female human or animal in need thereof comprising
administering to the human or the animal a nutritional, dietary, or food fatty acid supplement comprising:
at least 30% docosahexaenoic acid (DHA), by weight of the total fatty acids in the supplement in a form chosen from ethyl ester, free fatty acid, and triglyceride.

78. A method of delaying the onset of menopause in a female human or animal in need thereof comprising
administering to the human or the animal a nutritional, dietary, or food fatty acid supplement comprising:
at least 30% docosahexaenoic acid (DHA), by weight of the total fatty acids in the supplement in a form chosen from ethyl ester, free fatty acid, and triglyceride.

79. A method of decreasing the likelihood of birth defects comprising administering to a female human a nutritional, dietary, or food fatty acid supplement comprising:
at least 30% docosahexaenoic acid (DHA), by weight of the total fatty acids in the supplement in a form chosen from ethyl ester, free fatty acid, and triglyceride.

80. A method of decreasing the likelihood of fetal or infant mortality comprising
administering to a female human a nutritional, dietary, or food fatty acid supplement comprising:
at least 30% docosahexaenoic acid (DHA), by weight of the total fatty acids in the supplement in a form chosen from ethyl ester, free fatty acid, and triglyceride.

81. Use of a composition chosen from a nutritional supplement, a dietary supplement, a food supplement, a pharmaceutical grade supplement, and a medical food, for enhancing, improving, or increasing a female human's likelihood of becoming pregnant, comprising:
administering to the human the composition comprising:
at least 30% docosahexaenoic acid (DHA), by weight of the total fatty acids in the composition in a form chosen from ethyl ester, free fatty acid, and triglyceride.

82. The use according to paragraph 81, wherein the composition further comprises eicosapentaenoic acid (EPA) in a form chosen from ethyl ester, free fatty acid, and triglyceride.

83. The use according to paragraph 81 or 82, wherein the composition further comprises arachidonic acid in a form chosen from ethyl ester, free fatty acid, and triglyceride.

84. The use of according to paragraph 81, wherein the DHA is in the form of triglyceride.

85. The use according to paragraph 81, wherein the composition further comprises vitamin D.

86. The use according to paragraph 85, wherein the vitamin D is present in an amount ranging from about 400 to about 4000 International Units (IU), from about 1000 to about 4000 IU, or from about 2000 to about 4000 IU.

87. The use according to paragraph 85, wherein the composition further comprises at least one vitamin other than vitamin D.

88. The use according to paragraph 82, wherein the weight ratio of the DHA to the EPA ranges from about 500:1, 100:1, 50:1, 20:1, 15:1, 10:1, 9:1, 8:1, 7:1, 6:1, 5:1, 4:1, 3:1, 2:1, to 1:1.

89. The use according to paragraph 83, wherein the weight ratio of the omega-3 fatty acids to the omega-6 fatty acids is about 10:1 or greater.

90. The use according to paragraph 89, wherein the weight ratio of the omega-3 fatty acids to omega-6 fatty acids is about 20:1, 21:1, 22:1, 23:1, 24:1, 25:1 or greater.

91. The use according to paragraph 82, wherein DHA is present in an amount greater than EPA.

92. The use according to paragraph 91, wherein DHA is present in an amount ranging from about 500 mg to about 750 mg, and EPA is present in an amount ranging from about 80 mg to about 250 mg.

93. The use according to paragraph 92, wherein DHA:EPA are present in a weight ratio chosen from about 70:10, 500:200, and 600-750:150-250.

94. The use according to paragraph 82, wherein the composition comprises and from about 650 mg to about 750 mg DHA and from about 80 mg to about 130 mg EPA.

95. The use according to paragraph 81, wherein the composition comprises from about 750 mg to about 900 mg total omega-3 fatty acids.

96. The use according to paragraph 81, wherein the composition further comprises at least one antioxidant.

97. The use according to paragraph 96, wherein the at least one antioxidant is chosen from α-tocopherol (vitamin E), calcium disodium EDTA, alpha tocoferyl acetates, butylhydroxytoluenes (BHT), butylhydroxyanisoles (BHA), ascorbic acid and pharmaceutically acceptable salts and esters thereof, propyl gallate, citric acid and pharmaceutically acceptable salts thereof, malic acid and pharmaceutically acceptable salts thereof, and sulfite salts and mixtures thereof.

98. The use according to paragraph 97, wherein the at least one antioxidant comprises BHA.

99. The use according to paragraph 81, 82 or 83, wherein the fatty acid is derived from at least one oil chosen from marine oil, algae oil, plant-based oil, and microbial oil.

100. The use according to paragraph 99, wherein the oil is tuna fish oil.

101. The use according to paragraph 81, wherein the total omega-3 fatty acids are at least 70%, at least 75%, at least 80%, or at least 90%, by weight of the total fatty acids in the composition.

102. The use according to paragraph 82, wherein DHA and EPA are present in an amount chosen from about 35% to about 90% by weight of the total fatty acids in the composition, from about 40% to about 85% by weight of the total fatty acids in the composition, from about 40% to about 80% by weight of the total fatty acids in the composition, and from about 50% to about 80% by weight of the total fatty acids in the composition.

103. The use according to paragraph 81, wherein the composition comprises at least one other fatty acid other than DHA in a form chosen from ethyl ester, free fatty acid, and triglyceride.

104. The use according to paragraph 81, wherein the composition comprises at least one omega-3 fatty acid other than DHA chosen from those defined in the European Pharmacopoeia Omega-3 Triglycerides and the European Pharmacopoeia Omega-3 acid Ethyl Esters 60.

105. The use according to paragraph 81, wherein the composition further comprises: eicosapentaenoic acid (EPA) in a form chosen from ethyl ester, free fatty acid, and triglyceride, wherein DHA is present in an amount greater than EPA; and arachidonic acid in a form chosen from ethyl ester, free fatty acid, and triglyceride, wherein the weight ratio of omega-3 fatty acids to omega-6 fatty acids is 10:1 or greater.

106. The use according to paragraph 105, wherein the composition further comprises vitamin D.

107. The use according to paragraph 81, wherein the daily dosage per day of the total fatty acids in the composition ranges from 1 to 8 grams.

108. The use according to paragraph 107, wherein the daily dosage per day of the total fatty acids in the composition ranges from 2 to 4 grams.

109. The use according to paragraph 81, wherein DHA is present in an amount of at least 90% by weight of the total fatty acids in the composition.

110. The use according to paragraph 109, wherein the DHA is present in an amount of at least 95% by weight of the total fatty acids in the composition.

111. Use of a composition chosen from a nutritional supplement, a dietary supplement, a food supplement, a pharmaceutical grade supplement, and a medical food, for maintaining or improving oocyte and/or ovum quality in a female human in need thereof, comprising:
administering to the human the composition comprising:
at least 30% docosahexaenoic acid (DHA), by weight of the total fatty acids in the composition in a form chosen from ethyl ester, free fatty acid, and triglyceride.

112. The use according to paragraph 111, wherein the composition further comprises eicosapentaenoic acid (EPA) in a form chosen from ethyl ester, free fatty acid, and triglyceride.

113. The use according to paragraph 111 or 112, wherein the composition further comprises arachidonic acid in a form chosen from ethyl ester, free fatty acid, and triglyceride.

114. The use of according to paragraph 111, wherein the DHA is in the form of triglyceride.

115. The use according to paragraph 111, wherein the composition further comprises vitamin D.

116. The use according to paragraph 115, wherein the vitamin D is present in an amount ranging from about 400 to about 4000 International Units (IU), from about 1000 to about 4000 IU, or from about 2000 to about 4000 IU.

117. The use according to paragraph 115, wherein the composition further comprises at least one vitamin other than vitamin D.

118. The use according to paragraph 112, wherein the weight ratio of the DHA to the EPA ranges from about 500:1, 100:1, 50:1, 20:1, 15:1, 10:1, 9:1, 8:1, 7:1, 6:1, 5:1, 4:1, 3:1, 2:1, to 1:1.

119. The use according to paragraph 113, wherein the weight ratio of the omega-3 fatty acids to the omega-6 fatty acids is about 10:1 or greater.

120. The use according to paragraph 119, wherein the weight ratio of the omega-3 fatty acids to omega-6 fatty acids is about 20:1, 21:1, 22:1, 23:1, 24:1, 25:1 or greater.

121. The use according to paragraph 112, wherein DHA is present in an amount greater than EPA.

122. The use according to paragraph 121, wherein DHA is present in an amount ranging from about 500 mg to about 750 mg, and EPA is present in an amount ranging from about 80 mg to about 250 mg.

123. The use according to paragraph 122, wherein DHA: EPA are present in a weight ratio chosen from about 70:10, 500:200, and 600-750:150-250.

124. The use according to paragraph 112, wherein the composition comprises and from about 650 mg to about 750 mg DHA and from about 80 mg to about 130 mg EPA.

125. The use according to paragraph 111, wherein the composition comprises from about 750 mg to about 900 mg total omega-3 fatty acids.

126. The use according to paragraph 111, wherein the composition further comprises at least one antioxidant.

127. The use according to paragraph 126, wherein the at least one antioxidant is chosen from α-tocopherol (vitamin E), calcium disodium EDTA, alpha tocoferyl acetates, butylhydroxytoluenes (BHT), butylhydroxyanisoles (BHA), ascorbic acid and pharmaceutically acceptable salts and esters thereof, propyl gallate, citric acid and pharmaceutically acceptable salts thereof, malic acid and pharmaceutically acceptable salts thereof, and sulfite salts and mixtures thereof.

128. The use according to paragraph 127, wherein the at least one antioxidant comprises BHA.

129. The use according to paragraph 111, 112 or 113, wherein the fatty acid is derived from at least one oil chosen from marine oil, algae oil, plant-based oil, and microbial oil.

130. The use according to paragraph 129, wherein the oil is tuna fish oil.

131. The use according to paragraph 111, wherein the total omega-3 fatty acids are at least 70%, at least 75%, at least 80%, or at least 90%, by weight of the total fatty acids in the composition.

132. The use according to paragraph 112, wherein DHA and EPA are present in an amount chosen from about 35% to about 90% by weight of the total fatty acids in the composition, from about 40% to about 85% by weight of the total fatty acids in the composition, from about 40% to about 80% by weight of the total fatty acids in the composition, and from about 50% to about 80% by weight of the total fatty acids in the composition.

133. The use according to paragraph 111, wherein the composition comprises at least one other fatty acid other than DHA in a form chosen from ethyl ester, free fatty acid, and triglyceride.

134. The use according to paragraph 111, wherein the composition comprises at least one omega-3 fatty acid other than DHA chosen from those defined in the European Pharmacopoeia Omega-3 Triglycerides and the European Pharmacopoeia Omega-3 acid Ethyl Esters 60.

135. The use according to paragraph 111, wherein the composition further comprises: eicosapentaenoic acid (EPA) in a form chosen from ethyl ester, free fatty acid, and triglyceride, wherein DHA is present in an amount greater than EPA; and arachidonic acid in a form chosen from ethyl ester, free fatty acid, and triglyceride, wherein the weight ratio of omega-3 fatty acids to omega-6 fatty acids is 10:1 or greater.

136. The use according to paragraph 135, wherein the composition further comprises vitamin D.

137. The use according to paragraph 111, wherein the daily dosage per day of the total fatty acids in the composition ranges from 1 to 8 grams.

138. The use according to paragraph 137, wherein the daily dosage per day of the total fatty acids in the composition ranges from 2 to 4 grams.

139. The use according to paragraph 111, wherein DHA is present in an amount of at least 90% by weight of the total fatty acids in the composition.

140. The use according to paragraph 139, wherein the DHA is present in an amount of at least 95% by weight of the total fatty acids in the composition.

141. A method of enhancing or prolonging fertility in a subject, the method comprising;
administering a composition comprising an omega-3 fatty acid to a subject having a serum level ratio of omega-3 fatty acids to omega-6 fatty acids of 1:1 or less.

142. The method of Paragraph 141, further comprising determining the serum level ratio of omega-3 fatty acids to omega-6 fatty acids after administering the composition; and
administering additional doses of the composition comprising an omega-3 fatty acid when the subject is determined to have a serum level ratio of omega-3 fatty acids to omega-6 fatty acids of 1:1 or less.

143. The method of Paragraph 141, further comprising determining the serum level ratio of omega-3 fatty acids to omega-6 fatty acids; and
administering doses of the composition comprising an omega-3 fatty acid until the subject is determined to have a serum level ratio of omega-3 fatty acids to omega-6 fatty acids of greater than 1:1.

144. A method of enhancing or prolonging fertility in a subject, the method comprising;
administering a composition comprising an omega-3 fatty acid to a subject;
wherein the total fatty acid intake of the subject comprises a ratio of total omega-3 fatty acids to omega-6 fatty acids of 20:1 or greater.

145. The method of Paragraphs 141-144, further comprising initiating or continuing a treatment or procedure to enhance fertility of or impregnate the subject.

146. The method of any of Paragraphs 141-145, wherein the subject is a human female.

147. The method of Paragraph 146, wherein the subject is at least 30 years of age.

148. The method of Paragraph 147, wherein the subject is at least 35 years of age.

149. The method of any of Paragraphs 141-148, wherein the method comprises the further step of reducing the omega-6 fatty acid dietary intake of the subject.

150. The method of any of Paragraphs 141-149, wherein the method comprises the further step of instructing the subject to reduce their omega-6 fatty acid dietary intake.

151. The method of any of Paragraphs 141-150, wherein the composition comprising an omega-3 fatty acid comprises an omega-3 fatty acid selected from the group consisting of:
Hexadecatrienoic acid (HTA); α-Linolenic acid (ALA); Stearidonic acid (SDA); Eicosatrienoic acid (ETE); Eicosatetraenoic acid (ETA); Eicosapentaenoic acid (EPA); Heneicosapentaenoic acid (HPA); Docosapentaenoic acid (DPA); Clupanodonic acid; Docosahexaenoic acid (DHA); Tetracosapentaenoic acid; and Tetracosahexaenoic acid (Nisinic acid).

152. The method of any of Paragraphs 141-151, wherein the composition comprising omega-3 fatty acids is not a dietary supplement.

153. The method of any of Paragraphs 141-152, wherein the composition comprising omega-3 fatty acids is administered orally.

154. The method of any of Paragraphs 141-153, wherein the composition comprising omega-3 fatty acids is administered intravenously.

155. The method of any of Paragraphs 145-154, wherein the treatment or procedure to enhance fertility of or impregnate the subject is selected from the group consisting of:

stimulating follicles to cause unfertilized egg cells to develop; retrieving unfertilized egg cells from the subject; administering a fertility medication; in vitro fertilization; cryopreservation fertility treatments; and artificial insemination.

156. The method of any of Paragraphs 141-155, wherein the likelihood of birth defects is decreased.

157. The method of Paragraph 156, wherein the birth defect is Downs Syndrome.

158. The method of any of Paragraphs 141-157, wherein the likelihood of fetal or infant mortality is decreased.

159. The method of any of Paragraphs 141-158, wherein the subject is administered the composition comprising an omega-3 fatty acid for at least 1 week prior to the treatment or procedure.

160. The method of any of Paragraphs 141-159, wherein the subject is administered the composition comprising an omega-3 fatty acid for at least 1 month prior to the treatment or procedure.

161. The method of any of Paragraphs 141-160, wherein the subject is administered the composition comprising an omega-3 fatty acid for at least 3 months prior to the treatment or procedure.

162. The method of any of Paragraphs 141-161, whereby the onset of menopause is delayed.

163. A method of delaying the onset of menopause in a subject, the method comprising;

administering a composition comprising an omega-3 fatty acid to a subject having a serum level ratio of omega-3 fatty acids to omega-6 fatty acids of 1:1 or less.

164. The method of paragraph 163, wherein the subject is at least 25 years of age.

165. The method of paragraph 163, wherein the subject is at least 30 years of age.

166. The method of paragraph 163, wherein the subject is at least 35 years of age.

167. The method of any of paragraphs 163-166, wherein the composition comprising an omega-3 fatty acid is administered orally.

168. The method of any of paragraphs 163-167, further comprising determining the serum level ratio of omega-3 fatty acids to omega-6 fatty acids after administering the composition; and administering additional doses of the composition comprising an omega-3 fatty acid when the subject is determined to have a serum level ratio of omega-3 fatty acids to omega-6 fatty acids of 1:1 or less.

169. The method of any of paragraphs 163-168, further comprising determining the serum level ratio of omega-3 fatty acids to omega-6 fatty acids; and administering doses of the composition comprising an omega-3 fatty acid until the subject is determined to have a serum level ratio of omega-3 fatty acids to omega-6 fatty acids of greater than 1:1.

170. The method of any of paragraphs 163-169, wherein the total fatty acid intake of the subject comprises a ratio of total omega-3 fatty acids to omega-6 fatty acids of 20:1 or greater.

171. The method of any of paragraphs 163-170, further comprising initiating or continuing a treatment or procedure to enhance fertility of or impregnate the subject.

172. The method of any of paragraphs 163-171, wherein the subject is a human female.

173. The method of any of paragraphs 163-172, wherein the method comprises the further step of reducing the omega-6 fatty acid dietary intake of the subject.

174. The method of any of paragraphs 163-172, wherein the method comprises the further step of instructing the subject to reduce their omega-6 fatty acid dietary intake.

175. The method of any of paragraphs 163-174, wherein the composition comprising an omega-3 fatty acid comprises an omega-3 fatty acid selected from the group consisting of:

Hexadecatrienoic acid (HTA); α-Linolenic acid (ALA); Stearidonic acid (SDA); Eicosatrienoic acid (ETE); Eicosatetraenoic acid (ETA); Eicosapentaenoic acid (EPA); Heneicosapentaenoic acid (HPA); Docosapentaenoic acid (DPA); Clupanodonic acid; Docosahexaenoic acid (DHA); Tetracosapentaenoic acid; and Tetracosahexaenoic acid (Nisinic acid).

176. The method of any of paragraphs 163-175, wherein the treatment or procedure to enhance fertility of or impregnate the subject is selected from the group consisting of:

stimulating follicles to cause unfertilized egg cells to develop; retrieving unfertilized egg cells from the subject; administering a fertility medication; in vitro fertilization; cryopreservation fertility treatments; and artificial insemination.

177. The method of any of paragraphs 163-176, wherein the likelihood of birth defects is decreased.

178. The method of paragraph 176, wherein the birth defect is Down Syndrome.

179. The method of any of paragraphs 163-178, wherein the likelihood of fetal or infant mortality is decreased.

180. Use of a composition chosen from a nutritional supplement, a dietary supplement, a food supplement, a pharmaceutical grade supplement, and a medical food, for enhancing and/or prolonging fertility and/or reproductive function in a female human or animal in need thereof comprising administering to the human or the animal the composition comprising:

at least 30% docosahexaenoic acid (DHA), by weight of the total fatty acids in the composition in a form chosen from ethyl ester, free fatty acid, and triglyceride.

181. Use of a composition chosen from a nutritional supplement, a dietary supplement, a food supplement, a pharmaceutical grade supplement, and a medical food, for delaying the onset of menopause in a female human or animal in need thereof comprising administering to the human or the animal the composition comprising:

at least 30% docosahexaenoic acid (DHA), by weight of the total fatty acids in the composition in a form chosen from ethyl ester, free fatty acid, and triglyceride.

182. Use of a composition chosen from a nutritional supplement, a dietary supplement, a food supplement, a pharmaceutical grade supplement, and a medical food, for decreasing the likelihood of birth defects comprising administering to a female human the composition comprising:

at least 30% docosahexaenoic acid (DHA), by weight of the total fatty acids in the composition in a form chosen from ethyl ester, free fatty acid, and triglyceride.

183. Use of a composition chosen from a nutritional supplement, a dietary supplement, a food supplement, a pharmaceutical grade supplement, and a medical food, for decreasing the likelihood of fetal or infant mortality comprising administering to a female human the composition comprising:

at least 30% docosahexaenoic acid (DHA), by weight of the total fatty acids in the composition in a form chosen from ethyl ester, free fatty acid, and triglyceride.

EXAMPLES

Example 1

Mixed Fatty Acid Compositions

In a study, the following mixed fatty acid oil compositions will be tested together with 2000 or 4000 (IU) Vitamin D.

| Fatty acid oil mixture (w %) | EPA EE or TG content (w %) | DHA EE/TG content (w %) | Omega-3 (w %) | Vitamin D content (international units (iu) 1,25(OH)$_2$D$_3$) |
|---|---|---|---|---|
| Pronova DHA 10:70EE | 8-13% | 65-75% | 75-90% | 2000-4000 |
| Pure DHA (>95% DHA-EE) | less than 5% | >95% DHA-EE | at least 95% | 2000-4000 |
| Ultra Pure DHA (>97% DHA-EE and no EPA) | no EPA | >97% DHA-EE | at least 97% | 2000-4000 |
| Proinva 200:500 | | | | 2000-4000 |

EE = ethyl ester;
TG = triglyceride

Example 2

Consumption of Fatty Acids

The purpose of the experiments described herein is two-fold: 1) to evaluate the effect of a diet rich in omega-3 fatty acids on murine reproductive function and egg quality and, 2) to determine whether a diet rich in omega-3 fatty acids is safe for long-term consumption. As described herein, it was found that the lifelong consumption of omega-3 fatty acids maintains murine reproductive function at advanced maternal age and that the consumption of omega-3 fatty acids at the time of the normal rapid decline in murine reproductive function results in a significant improvement in oocyte quality. Additionally, omega-3 fatty acids were found to be safe for long-term consumption over multiple generations without any evidence of essential fatty acid deficiency. These findings have implications for both successful natural and assisted reproduction at advanced maternal age.

Results

Reproductive and Fertility Outcomes in Long-Term Studies

It was first sought to evaluate the effect of the long-term consumption of either omega-3 or omega-6 fatty acids on reproductive function. To this end, an omega-3 fatty acid rich diet was designed to mimic the fatty acid composition of cold water fish (Le H D, Meisel J A, de Meijer V E, Fallon E M, Gura K M, Nose V, Bistrian B R, Puder M (2011). Docosahexaenoic Acid and Arachidonic Acid Prevent Essential Fatty Acid Deficiency and Hepatic Steatosis. *JPEN J Parenter Enteral Nutr.*), with an omega-3 to omega-6 fatty acid ratio of 20:1 provided as docosahexaenoic acid (DHA; 22:6n-3; omega-3 fatty acid) and arachidonic acid (AA; 20:4n-6; omega-6 fatty acid). In contrast an omega-6 fatty acid rich diet was designed to mimic the standard western diet, with fat provided as soybean oil and thus containing an omega-6 to omega-3 fatty acid ratio of approximately 8:1 provided as linoleic acid (LA; 18:2n-6; omega-6 fatty acid) and alpha-linolenic acid (ALA; 18:3n-3; omega-3 fatty acid). A third diet in which all fat was provided as hydrogenated coconut oil (HCO), which is deficient in essential fatty acids, was used as a control for essential fatty acid deficiency. Further details regarding these three isocaloric diets are presented in Table 1.

TABLE 1

Composition of Experimental Diets

| | HCO | SOY | DHA |
|---|---|---|---|
| Casein | 501.2 | 501.2 | 501.2 |
| L-Cystine | 7.2 | 7.2 | 7.2 |

TABLE 1-continued

Composition of Experimental Diets

| | HCO | SOY | DHA |
|---|---|---|---|
| Sucrose | 400 | 400 | 400 |
| Cornstarch | 1676.5 | 1676.5 | 1676.3 |
| Dyetrose | 589 | 589 | 589 |
| Mineral Mix #210050 | 29.4 | 29.4 | 29.4 |
| Vitamin Mix #310025 | 38.7 | 38.7 | 38.7 |
| Hydrogenated Coconut Oil | 360 | 0 | 284.4 |
| Soybean Oil | 0 | 360 | 0 |
| Docosahexaenoic Acid (DHA) | 0 | 0 | 72 |
| Arachidonic Acid (AA) | 0 | 0 | 3.6 |
| Total | 3602.0 | 3602.0 | 3601.8 |

All values reported as kcal/kg diet.

Figure 1B:
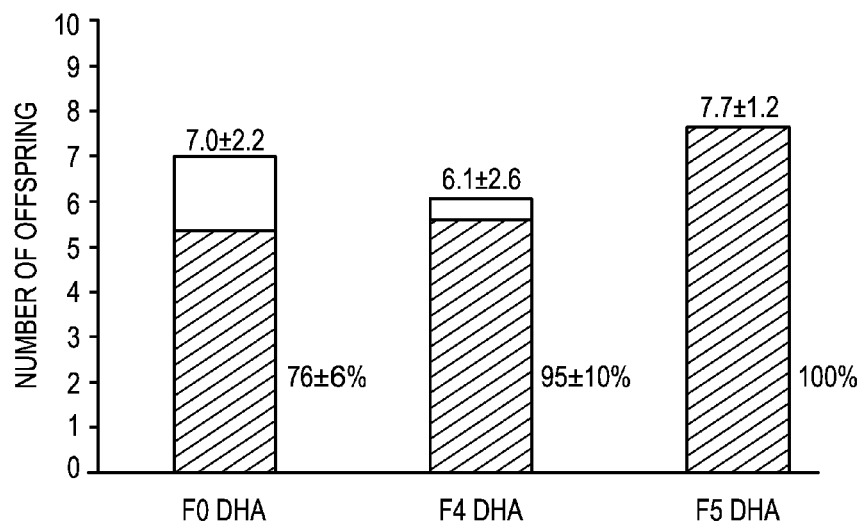

Prior to evaluating reproductive potential at advanced maternal age, breeding trials were performed to characterize the reproductive potential of animals on these diets during the normal murine female reproductive lifespan. To do this, adult female mice were randomized to one of the three different isocaloric diets (HCO, SOY, DHA). Following 4 weeks of dietary treatment, breeding trials were initiated on this F0 generation with subsequent generations of animals being maintained on the same diet and breeding trials being continued with each subsequent generation as females attained reproductive maturity. The litter size and viability of F1 generation animals (born to F0 dams) in each of the experimental diet groups did not differ (see FIG. 1A, which depicts a graph of litter size and viability which were not different between F0 generation animals in each of the diet groups (N=3, 6, 3 litters for SOY, HCO and DHA groups, respectively); offspring viability was assessed at 3 weeks.). Animals on the SOY diet were bred to the F3 generation and animals on the DHA diet were bred to the F6 generation at which time further breeding attempts were terminated. Notably, despite continued attempts at breeding, animals on the HCO diet were not able to successfully reproduce beyond the F1 generation likely secondary to severe essential fatty acid deficiency, defined as a triene:tetraene (T:T) ratio of >0.2 on the serum fatty acid profile (Table 2). Successive generations of animals on the DHA diet continued to have litter sizes within the expected range with a notable improvement in offspring survival in later generations; from 75% in the F1 generation to 95% in the F5 generation and 100% in the F6 generation (see FIG. 1B, which depicts a graph of reproductive function maintained over 6 successive generations of animals on the DHA diet with an improvement in viability over successive generations (N=3, 13, 3 litters for F0, F4 and F5 generations, respectively); offspring viability was assessed at 3 weeks.).

TABLE 2

Serum fatty acid profiles of F1 generation animals on the HCO, SOY and DHA diets.

| Fatty acid | HCO (N = 4) | SOY (N = 5) | DHA (N = 5) | P |
|---|---|---|---|---|
| Saturated Fats | | | | |
| Tetradecanoic (myristic) acid, 14:0 | 1.346 ± 0.142 | 0.688 ± 0.492 | 1.177 ± 0.675 | 0.359 |
| Hexadecanoic (palmitic) acid, 16:0 | 20.269 ± 1.370 | 20.765 ± 2.361 | 24.036 ± 1.029 | 0.016 |
| Octadecanoic (stearic) acid, 18:0 | 7.381 ± 0.370 | 9.863 ± 0.969 | 7.049 ± 0.596 | 0.013 |
| Monounsaturated Fats | | | | |
| Hexadecenoic (palmitoleic) acid, 16:1ω7 | 8.308 ± 0.782 | 2.936 ± 1.383 | 6.412 ± 1.023 | 0.005 |
| Octadecenoic (vaccenic) acid, 18:1ω7 | 4.900 ± 0.470 | 1.827 ± 0.496 | 0.998 ± 0.149 | 0.003 |
| Octadecenoic (oleic) acid, 18:1ω9 | 22.766 ± 1.252 | 14.935 ± 3.228 | 15.493 ± 1.067 | 0.009 |
| Polyunsaturated Fats | | | | |
| Octadecatrienoic (alpha-linolenic) acid, 18:3ω3 | 0.004 ± 0.010 | 0.159 ± 0.050 | 0 | 0.004 |
| Eicosapentaenoic (trimnodonic)acid, 20:5ω3 | 0.078 ± 0.012 | 0.229 ± 0.057 | 5.558 ± 0.638 | 0.003 |
| Docosapentaenoic (clupanodonic) acid, 2:5ω3 | 0.089 ± 0.022 | 0.226 ± 0.162 | 0.538 ± 0.061 | 0.008 |
| Docosahexaenoic acid, 22:6ω3 | 2.865 ± 0.301 | 9.215 ± 2.264 | 24.949 ± 2.791 | 0.003 |
| Octadecadienoic (linoleic) acid, 18:2ω6 | 8.380 ± 0.451 | 17.464 ± 0.968 | 5.950 ± 0.346 | 0.003 |
| Octadecatrienoic (gamma-linolenic) acid, 8:3ω6 | 0.221 ± 0.140 | 0.199 ± 0.167 | 0 | 0.009 |
| Eicosatrienoic (dihomo-gamma-linolenic) acid, 20:3ω6 | 1.611 ± 0.094 | 0.899 ± 0.353 | 0.132 ± 0.081 | 0.003 |
| Eicosatetraenoic (arachidonic) acid, 20:4ω6 | 8.795 ± 0.586 | 19.502 ± 5.444 | 6.409 ± 0.317 | 0.003 |
| Eicosatrienoic (mead) acid, 20:3ω9 | 9.370 ± 1.002 | 0.123 ± 0.044 | 0.018 ± 0.039 | 0.004 |
| Totals | | | | |
| Total ω3 | 3.036 ± 0.287 | 9.829 ± 2.357 | 31.045 ± 2.338 | 0.003 |
| Total ω6 | 19.048 ± 0.859 | 38.276 ± 5.402 | 12.491 ± 0.315 | 0.003 |
| Total ω9 | 32.545 ± 1.451 | 15.131 ± 3.183 | 15.688 ± 1.067 | 0.010 |
| Total ω-7 | 5.134 ± 0.533 | 1.827 ± 0.496 | 1.032 ± 0.192 | 0.003 |
| Total saturated FA | 30.856 ± 1.004 | 31.849 ± 2.921 | 33.333 ± 1.452 | 0.113 |
| Total monounsaturated FA | 36.617 ± 1.436 | 19.772 ± 5.039 | 23.114 ± 1.119 | 0.008 |
| Total polyunsaturated FA | 32.527 ± 0.902 | 48.380 ± 7.698 | 43.553 ± 2.336 | 0.008 |
| Ratios | | | | |
| Triene:Tetraene ratio | 1.072 ± 0.170 | 0.006 ± 0.002 | 0.003 ± 0.006 | 0.006 |
| ω6/ω3 ratio | 6.305 ± 0.440 | 3.981 ± 0.484 | 0.404 ± 0.033 | 0.003 |

All values represent percent ± SD.

Figure 2A:
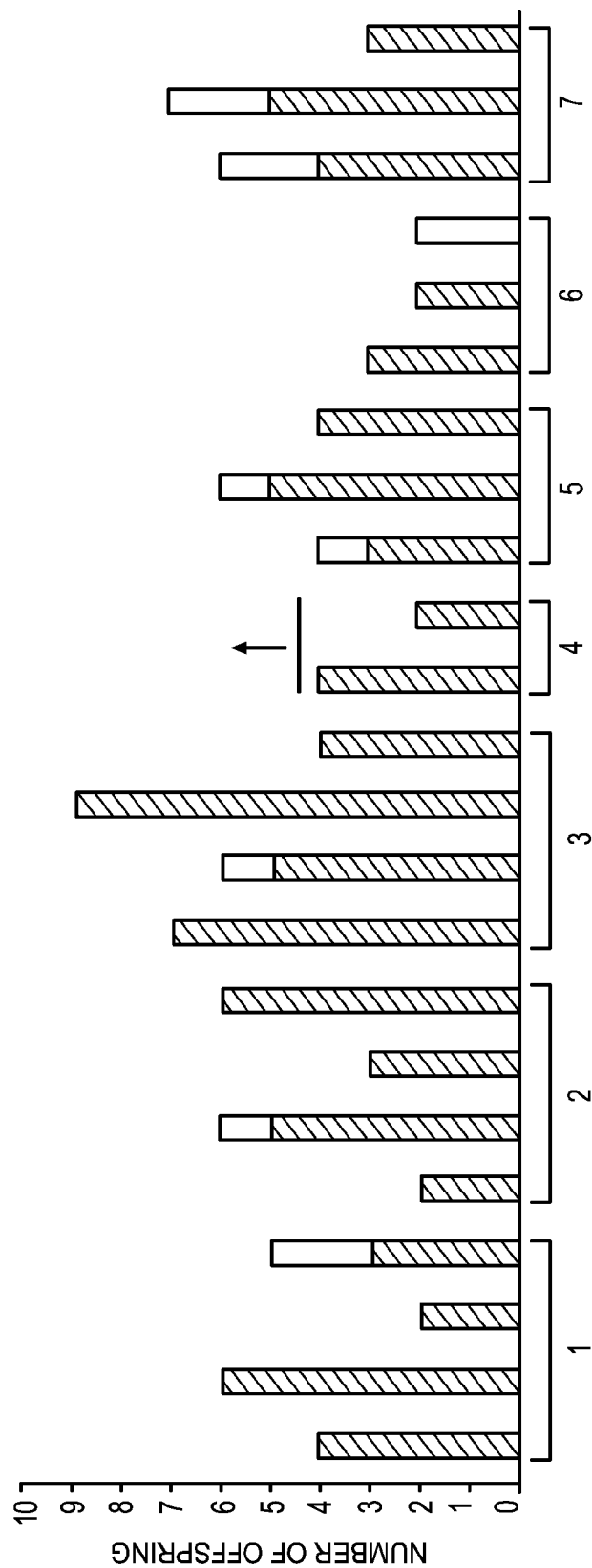
FIGS. 2A, 2B, and 2C are graphs of reproductive and fertility outcomes in long-term diet studies at advanced murine maternal reproductive age (10-15 months), as described in Example 2.
Figure 2B:
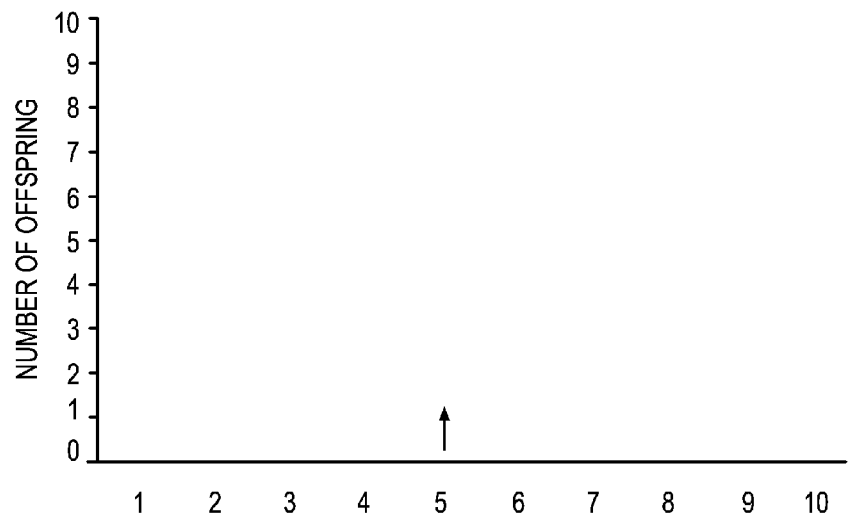
Figure 2C:
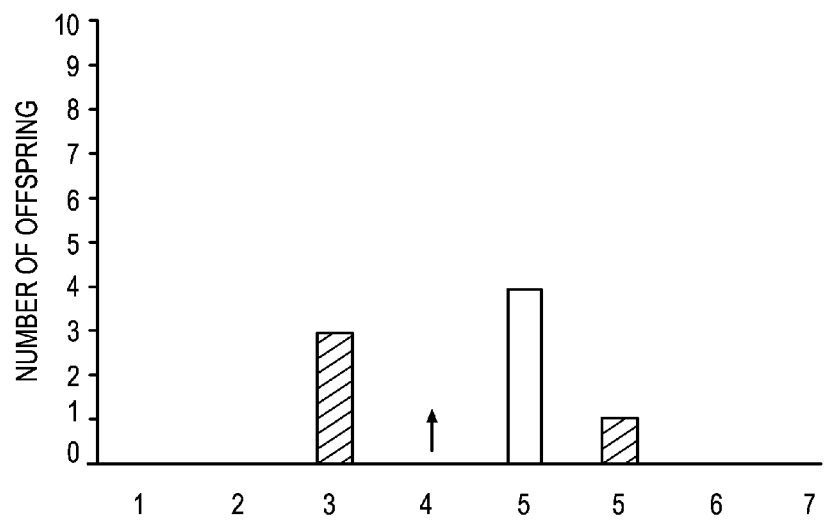

Once the ability of animals on the omega-3 and omega-6 rich diets to successfully breed within the normal female reproductive lifespan had been confirmed, animals on these diets were then tested for their ability to reproduce at advanced maternal age (>10 months of age). All animals on the omega-3 rich diet (N=7) were able to successfully reproduce with an average of 3.3±0.3 litters/animal between 10 and 15 months of age (see FIG. 2A, which depicts a graph of reproductive function maintained in females on the DHA diet at advanced maternal age; offspring viability was assessed at 2 weeks. Each animal is indicated by a number on the x-axis and each bar represents one litter. White bars represent total number of offspring and black bars represent viable offspring. Crosses indicate animals that died or had to be euthanized during the study period.). Although the average litter was smaller (4.4±1.9 offspring/litter) for dams at advanced maternal age (>10 months) compared to younger cohorts of animals (6.0±2.7 offspring/litter) on the same diet (P=0.10), the overall survival of the offspring born to dams at advanced maternal age was remarkably high at 89%. In stark contrast, none of the 10 aged animals maintained on the omega-6 rich diet had any viable litters (see FIG. 2B, which demonstrates that animals on the SOY diets had very poor reproductive success at advanced maternal age; offspring viability was assessed at 2 weeks). As another point of comparison, breeding trials at 10 months of age were also initiated for animals on a standard laboratory rodent chow (N=7). The reproductive success of these animals also contrasted starkly to those on the omega-3 rich diet, with only 2 animals having 1 viable litter each (see FIG. 2C, which demonstrates that animals on CHOW diets had very poor reproductive success at advanced maternal age; offspring viability was assessed at 2 weeks). These findings suggest that the remarkable increase in dietary omega-6 fatty acids in the human diet over the last 100 years may actually be detrimental to the reproductive success of women of advanced maternal age (Eaton S B, Konner M (1985). Paleolithic nutrition. A consideration of its nature and current implications. *N Engl J. Med.* 312, 283-289; Simopoulos A P (2003). Importance of the ratio of omega-6/omega-3 essential fatty acids: evolutionary aspects. *World Rev Nutr Diet.* 92, 1-22; Simopoulos A P (2006). Evolutionary aspects of diet, the omega-6/omega-3 ratio and genetic variation: nutritional implications for chronic diseases. *Biomed Pharmacother.* 60, 502-507; Simopoulos A P (2009). Evolutionary aspects of the dietary omega-6:omega-3 fatty acid ratio: medical implications. *World Rev Nutr Diet.* 100, 1-21; Simopoulos A P (2011). Importance of the omega-6/omega-3 balance in health and disease: evolutionary aspects of diet. *World Rev Nutr Diet.* 102, 10-21).

Oocyte Quality in Acute Dietary Treatment Studies

An acute dietary treatment model was next investigated. Since egg quality is recognized as the single most important factor for determining the success of pregnancy for women of advanced reproductive age (Navot D, Bergh P A, Williams M, Garrisi G J, Guzman I, Sandler B, Fox J, Schreiner-Engel P, Hofmann G E, Grunfeld L (1991a). An insight into early reproductive processes through the in vivo model of ovum donation. *J Clin Endocrinol Metab.* 72, 408-414; Navot D, Bergh P A, Williams M A, Garrisi G J, Guzman I, Sandler B, Grunfeld L (1991b). Poor oocyte quality rather than implantation failure as a cause of age-related decline in female fertility. *Lancet.* 337, 1375-1377), the aim was to determine the effect of acute dietary treatment on oocyte quality at advanced maternal age.

Figure 3A:
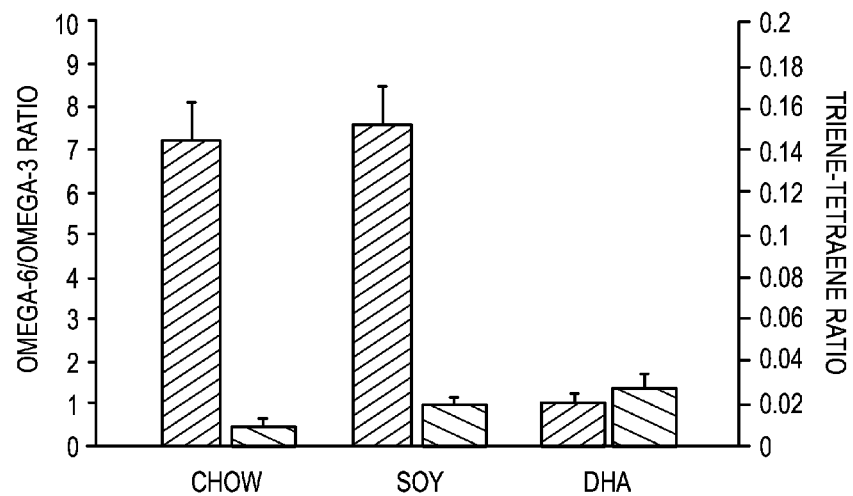
FIGS. 3A, 3B, 3C, 3D, and 3E depict fatty acid profiles, ovarian follicle counts and oocyte quality in acute dietary treatment studies, as described in Example 2. In particular.
Figure 5A:
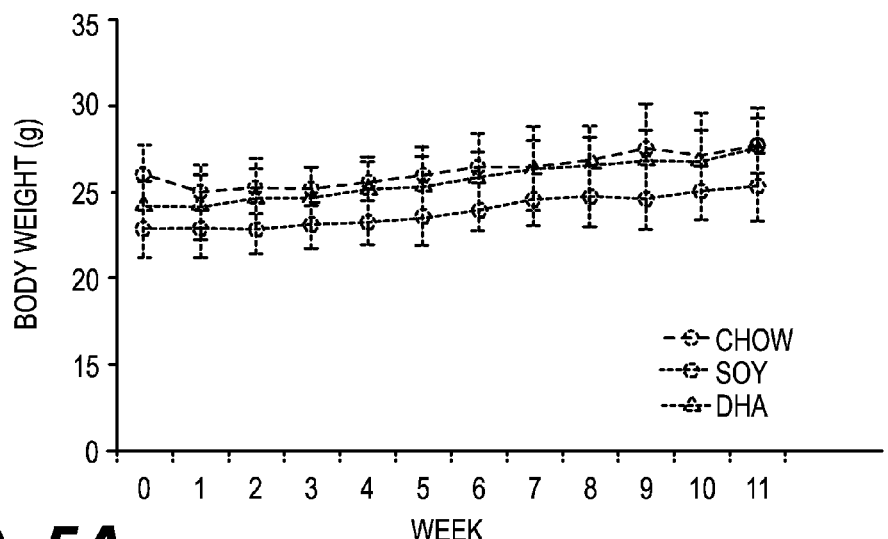
FIGS. 5A and 5B are graphs of animal growth and diet consumption in acute dietary treatment, as described in Example 2.
Figure 5B:
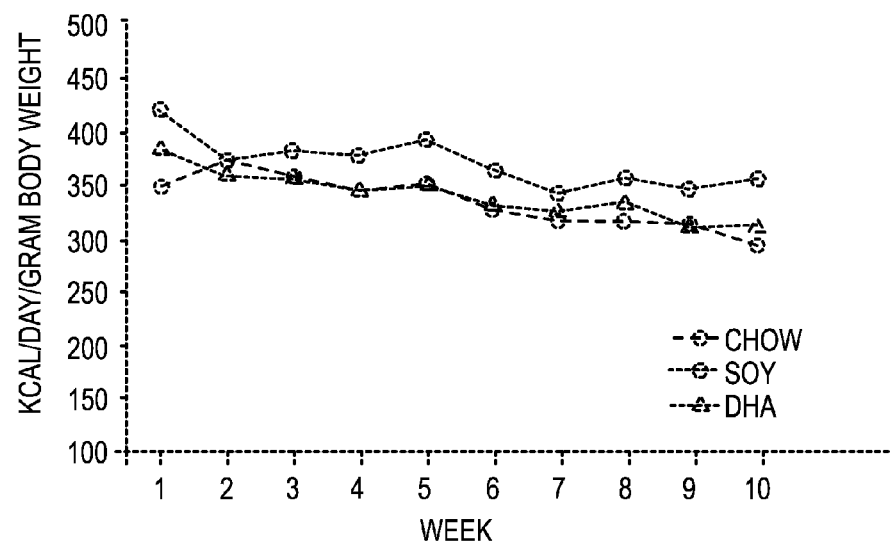

Thirty-six 10-month old virgin female mice fed a standard laboratory rodent chow (CHOW) until 10 months of age were randomly assigned to each of 3 different diet groups (N=12 CHOW, N=12 SOY, N=12 DHA). One animal on the SOY diet necessitated euthanasia during week 10 of dietary treatment due to severe dermatitis. The remaining 35 animals survived to complete the 12-week dietary treatment and were euthanized at 13 months of age. There were no differences in the average calories consumed or the average weekly animal body weights between groups (see FIGS. 5A and 5B, which show no difference in (FIG. 5A) body weights or (FIG. 5B) kcal consumed at any time point spanning the 11-week study; all data are represented as mean±SD). The acute dietary treatment did not result in the development of biochemical essential fatty acid deficiency in any diet group (Table 3). However, even with this relatively short period of dietary treatment, the serum omega-6/omega-3 fatty acid ratio was significantly higher in the DHA diet group compared to both the CHOW and SOY diet groups (see FIG. 3A, which depicts a graph of serum omega-6/omega-3 fatty acid and triene:tetraene ratios of animals in each acute dietary treatment group. The serum omega-6/omega-3 fatty acid ratio was more than 7-fold lower in the DHA group compared to the CHOW ($P=0.008$) and SOY ($P=0.008$) groups and, no animal in any diet group had evidence of biochemical essential fatty acid deficiency (triene:tetraene ratio>0.2) (N=5, 5, 5 animals for CHOW, SOY and DHA groups, respectively). All bars indicate mean±SD.).

TABLE 3

Serum fatty acid profiles of aged animals following acute dietary treatment with the CHOW, SOY or DHA diet

| Fatty acid | HCO (N = 4) | SOY (N = 5) | DHA (N = 5) | P |
|---|---|---|---|---|
| Saturated Fats | | | | |
| Tetradecanoic (myristic) acid, 14:0 | 0.568 ± 0.084 | 0.510 ± 0.057 | 1.162 ± 0.396 | 0.007 |
| Hexadecanoic (palmitic) acid, 16:0 | 34.939 ± 0.496 | 34.105 ± 3.256 | 33.488 ± 9.150 | 0.357 |
| Octadecanoic (stearic) acid, 18:0 | 17.912 ± 1.544 | 19.879 ± 1.331 | 22.826 ± 4.556 | 0.054 |
| Monounsaturated Fats | | | | |
| Hexadecenoic (palmitoleic) acid, 16:1ω7 | 2.091 ± 0.356 | 2.342 ± 0.256 | 3.247 ± 0.863 | 0.090 |
| Octadecenoic (vaccenic) acid, 18:1ω7 | 1.218 ± 0.105 | 1.558 ± 0.482 | 1.311 ± 0.240 | 0.326 |
| Octadecenoic (oleic) acid, 18:1ω9 | 9.976 ± 1.422 | 11.301 ± 1.436 | 11.617 ± 2.483 | 0.275 |
| Polyunsaturated Fats | | | | |
| Octadecatrienoic (alpha-linolenic) acid, 18:3ω3 | 0.552 ± 0.181 | 0.217 ± 0.032 | 0.030 ± 0.006 | 0.002 |
| Eicosapentaenoic (trimnodonic) acid, 20:5ω3 | 1.112 ± 0.125 | 0.363 ± 0.069 | 4.865 ± 0.792 | 0.002 |
| Docosapentaenoic (clupanodonic) acid, 2:5ω3 | 0.147 ± 0.018 | 0.060 ± 0.017 | 0.159 ± 0.036 | 0.008 |
| Docosahexaenoic acid, 22:6ω3 | 2.253 ± 0.261 | 2.759 ± 0.556 | 7.282 ± 1.245 | 0.005 |
| Octadecadienoic (linoleic) acid, 18:2ω6 | 22.114 ± 1.098 | 13.774 ± 1.334 | 7.778 ± 1.289 | 0.002 |
| Octadecatrienoic (gamma-linolenic) acid, 8:3ω6 | 0.107 ± 0.020 | 0.160 ± 0.094 | 0.006 ± 0.014 | 0.016 |
| Eicosatrienoic (dihomo-gamma-linolenic) acid, 20:3ω6 | 0.572 ± 0.032 | 0.813 ± 0.171 | 0.299 ± 0.055 | 0.002 |

TABLE 3-continued

Serum fatty acid profiles of aged animals following acute dietary treatment with the CHOW, SOY or DHA diet

| Fatty acid | HCO (N = 4) | SOY (N = 5) | DHA (N = 5) | P |
|---|---|---|---|---|
| Eicosatetraenoic (arachidonic) acid, 20:4ω6 | 5.693 ± 0.773 | 10.998 ± 1.547 | 4.793 ± 0.315 | 0.003 |
| Eicosatrienoic (mead) acid, 20:3ω9 | 0.047 ± 0.012 | 0.217 ± 0.051 | 0.130 ± 0.037 | 0.003 |
| Totals | | | | |
| Total ω3 | 3.952 ± 0.472 | 3.399 ± 0.635 | 12.335 ± 1.594 | 0.005 |
| Total ω6 | 28.626 ± 1.043 | 25.868 ± 2.801 | 12.914 ± 1.408 | 0.005 |
| Total ω9 | 10.302 ± 1.375 | 11.919 ± 1.673 | 12.228 ± 2.824 | 0.228 |
| Total ω-7 | 1.259 ± 0.097 | 1.617 ± 0.470 | 1.392 ± 0.309 | 0.230 |
| Total saturated FA | 53.742 ± 1.828 | 52.767 ± 4.370 | 57.871 ± 4.702 | 0.395 |
| Total monounsaturated FA | 13.605 ± 1.739 | 15.661 ± 2.187 | 16.750 ± 3.823 | 0.395 |
| Total polyunsaturated FA | 32.653 ± 1.297 | 29.572 ± 3.344 | 25.378 ± 2.413 | 0.016 |
| Ratios | | | | |
| Triene:Tetraene ratio | 0.009 ± 0003 | 0.020 ± 0.002 | 0.027 ± 0.007 | 0.005 |
| ω6/ω3 ratio | 7.318 ± 0.830 | 7.749 ± 1.149 | 1.057 ± 0.144 | 0.009 |

All values represent percent ± SD.

Figure 3B:
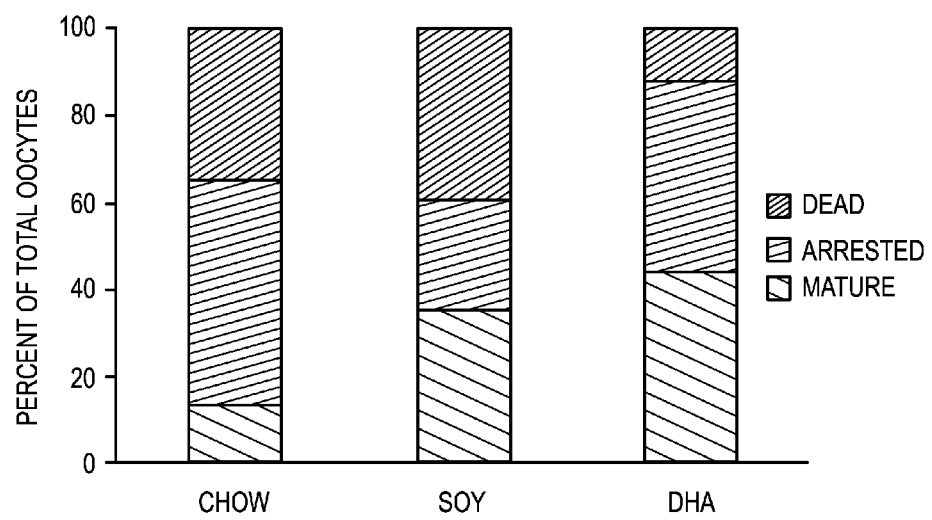
Figure 3C:
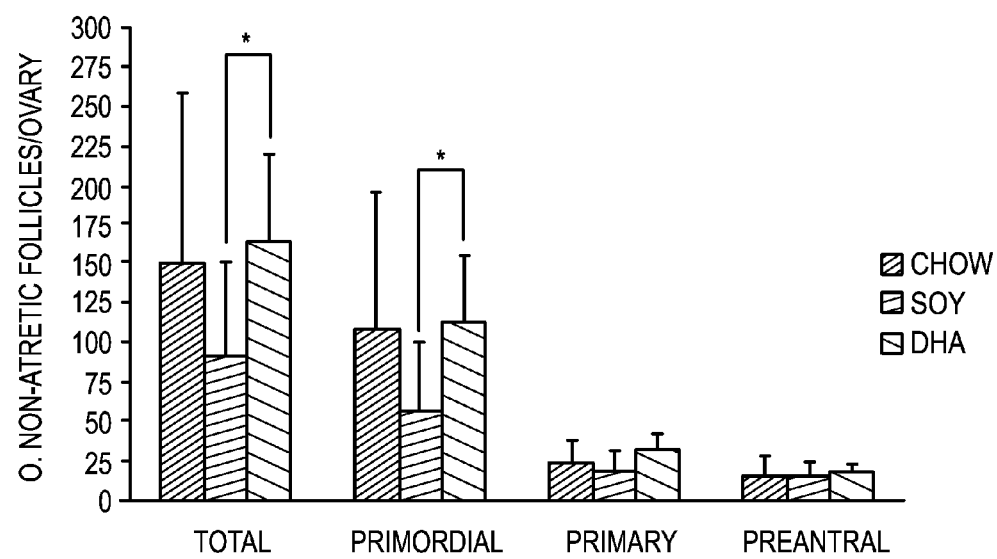

Oocyte yield following hormonal stimulation in addition to the oocyte maturational status and quality were evaluated for the 35 female mice that survived to 13 months of age. A total of 53 oocytes were collected from CHOW fed animals compared to 23 and 25 for the SOY and DHA diet groups, respectively. On evaluation of oocyte maturational status, a greater percentage of the oocytes harvested from animals on the DHA diet (44%) were found to be fully mature (MII stage), representing the fertilization-competent egg pool, compared to oocytes from animals on the CHOW (13%) and SOY (35%) diets (P=0.01). Additionally, only 12% of oocytes from animals on the DHA diet were atretic as compared to 39% and 35% of oocytes from animals the SOY and CHOW diets, respectively (P=0.09) (see FIG. 3B, which depicts a graph of oocyte characterization demonstrating that a larger percentage of oocytes from animals in the DHA group were fully mature and fewer were atretic compared to the CHOW and SOY groups (N=53, 23 and 25 oocytes for CHOW, SOY and DHA groups, respectively). All bars indicate mean±SD.). Similarly, ovarian follicle counts demonstrated that the number of primordial and total non-atretic follicles were significantly lower in ovaries from animals on the SOY diet compared to animals on the DHA diet (see FIG. 3C, which depicts a graph of ovarian follicle counts demonstrating a greater number of total (P=0.04) and primordial follicles (P=0.04) in ovaries from animals following acute treatment with the DHA diet compared to the SOY diet (N=6, 6 and 7 animals for CHOW, SOY and DHA groups, respectively). All bars indicate mean±SD.).

Figure 3D:
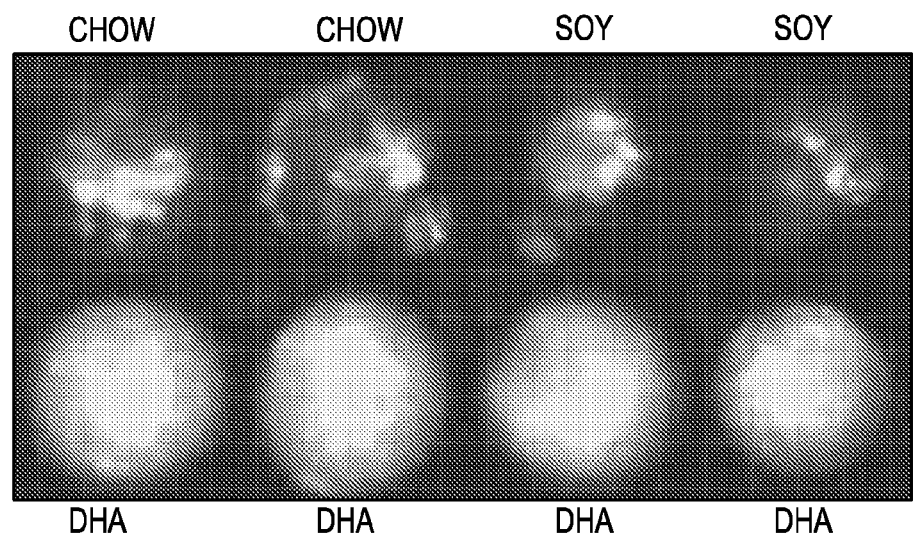
Figure 3E:
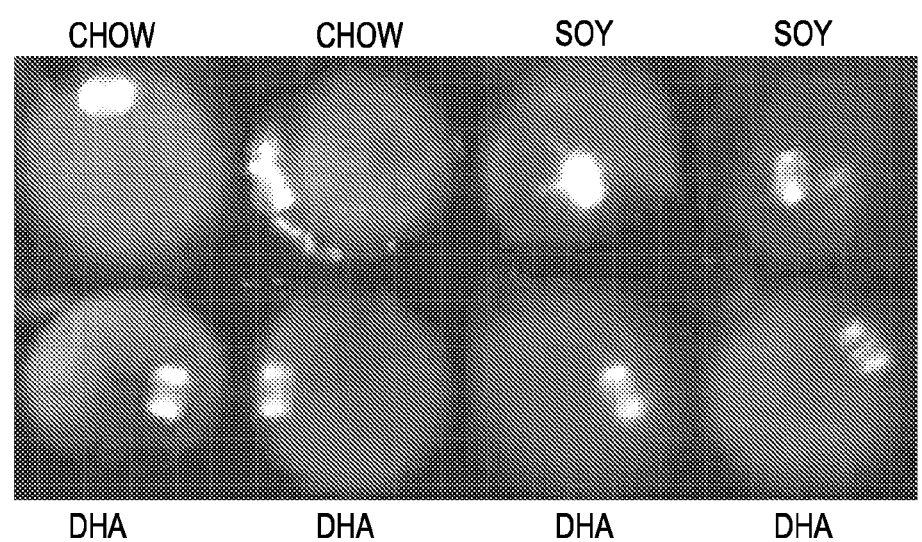

The quality of the fully mature (MII stage) oocytes collected from animals in each of the 3 diet groups was evaluated. Fully mature oocytes were selected for this analysis because age-related defects in oocytes are clearly evident at this maturation stage and because these oocytes represent the fertilization-competent egg pool. Oocyte quality was evaluated by assessing mitochondrial staining pattern and spindle integrity with individual oocytes randomly assigned to each of these endpoints. Mitochondrial aggregation has been linked to the decline in coyote quality with advanced maternal age and a uniform cytoplasmic distribution of mitochondria without aggregation is indicative of a good quality oocyte (Tarin J J, Perez-Albala S, Cano A (2001). Cellular and morphological traits of oocytes retrieved from aging mice after exogenous ovarian stimulation. *Biol Reprod.* 65, 141-150). Confocal analysis of the mitochondria revealed that although mitochondria had a uniform cytoplasmic distribution pattern in 6/6 (100%) MII oocytes from animals on the DHA diet, there was extensive mitochondrial aggregation in oocytes from animals in the other diet groups with 1/3 (33%) MII oocytes from animals on the SOY diet and 0/4 (0%) MII oocytes from animals on the CHOW diet being classified as normal (P=0.006) (see FIG. 3D, which depicts a photomicrographic image of representative mitochondrial staining of oocytes obtained from animals in each of the acute dietary treatment groups. Mitochondria appeared normal in 6/6 (100%) mature oocytes from animals in the DHA group, compared to 0/4 (0%) and 1/3 (33%) mature oocytes in the CHOW and SOY diet groups, respectively (P=0.006)). Similarly, confocal analysis of α-tubulin and DNA distribution revealed that meiotic spindles in ⅘ (80%) MII oocytes collected from DHA animals were regular in shape and size with distinct microtubule morphology. In contrast, 0/5 (0%) and ⅔ (66%) MII oocytes from SOY and CHOW fed animals, respectively, had normal meiotic spindles (P=0.03) (see FIG. 3E, which depicts a photomicrographic image of representative tubulin (spindle apparatus, green) and DNA (blue) staining of oocytes obtained from animals in each of the acute dietary treatment groups. Meiotic spindles appeared normal in ⅘ (80%) mature oocytes from animals in the DHA group as compared to ⅔ (66%) and 0/5 (0%) mature oocytes from animals in the CHOW and SOY groups, respectively (P=0.03)).

Safety Evaluation

The omega-3 fatty acid rich diet associated with the beneficial reproductive effects in this study provided 2% of total calories in the form of the omega-3 fatty acid DHA. This diet does not contain any of the traditional essential fatty acids, ALA and LA (Burr G O, Burr M M (1973). Nutrition classics from The Journal of Biological Chemistry 82:345-67, 1929. A new deficiency disease produced by the rigid exclusion of fat from the diet. *Nutr Rev.* 31, 248-249), but rather contains downstream molecules in the omega-3 and omega-6 fatty acid pathways (DHA and AA). As such, the aim was to determine whether animals maintained on the omega-3 rich diet developed any biochemical or clinical evidence of essential fatty acid deficiency. Clinically essential fatty acid deficiency results in compromised growth, reproduction and lactation (Burr G O, Burr M M (1973). Nutrition classics from The Journal of Biological Chemistry 82:345-67, 1929. A new deficiency disease produced by the rigid exclusion of fat from the diet. *Nutr Rev.* 31, 248-249). Since it has already been confirmed the ability of animals on the omega-3 rich diet to reproduce and lactate successfully over multiple generations, growth patterns were used as an additional clinical indicator of essential fatty acid deficiency and on serum fatty acid profiles to evaluate for biochemical essential fatty acid deficiency. Lastly, histologic evaluation of all major organ systems was performed.

Fatty Acid Profiles

Figure 4A:
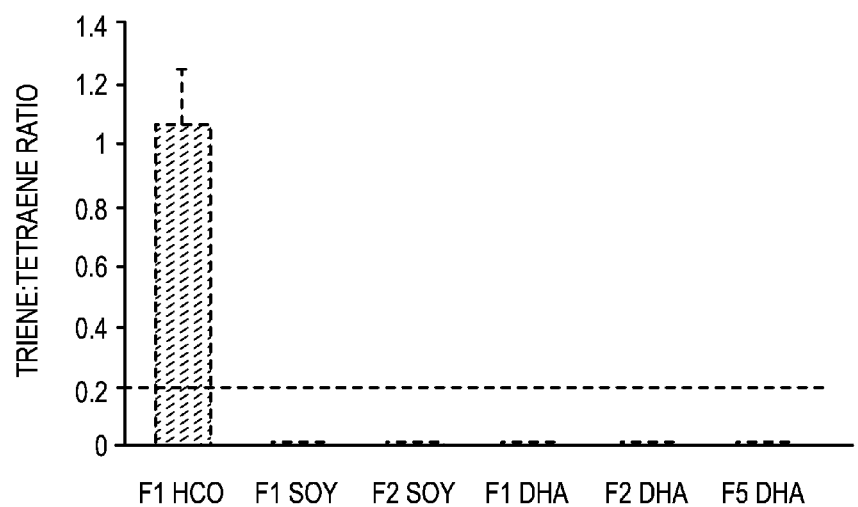
FIGS. 4A, 4B, 4C, 4D, 4E, 4F, 4G, and 4H are graphs demonstrating the evaluation of safety of the omega-3 rich diet with fatty acid profiles and growth, as described in Example 2. In particular.

No animals in either the SOY (F1 or F2 generation) or the DHA (F1, F2 or F5 generation) diet groups had any evidence of biochemical essential fatty acid deficiency. In contrast, all animals on the HCO diet had evidence of biochemical essential fatty acid deficiency with consistently elevated serum T:T ratios (see FIG. 4A, in which serum triene:tetraene ratios demonstrate that no animals on the SOY or DHA diet had evidence of biochemical essential fatty acid deficiency (triene:tetraene ratio>0.2, horizontal dashed line). All data represented as mean±SD.). These findings can be confirmed by the mead acid (20:3n-9; omega-9 fatty acid), as there is a relative overproduction of mead acid in the setting of essential fatty acid deficiency. Mead acid accounted for 9.37±1.00% of the total fatty acid content in the F1 HCO group as compared to only 0.12±0.04% in the F1 SOY and 0.02±0.04% in the F1 DHA group.

Figure 4B:
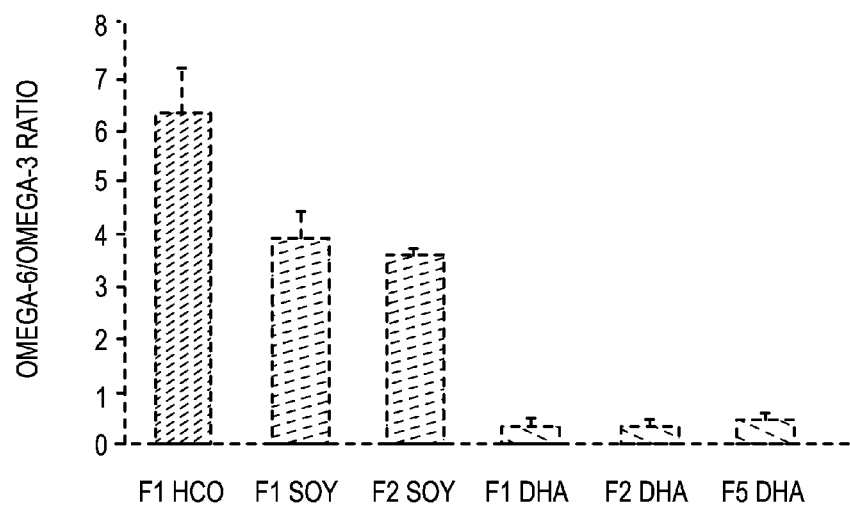
Figure 4C:
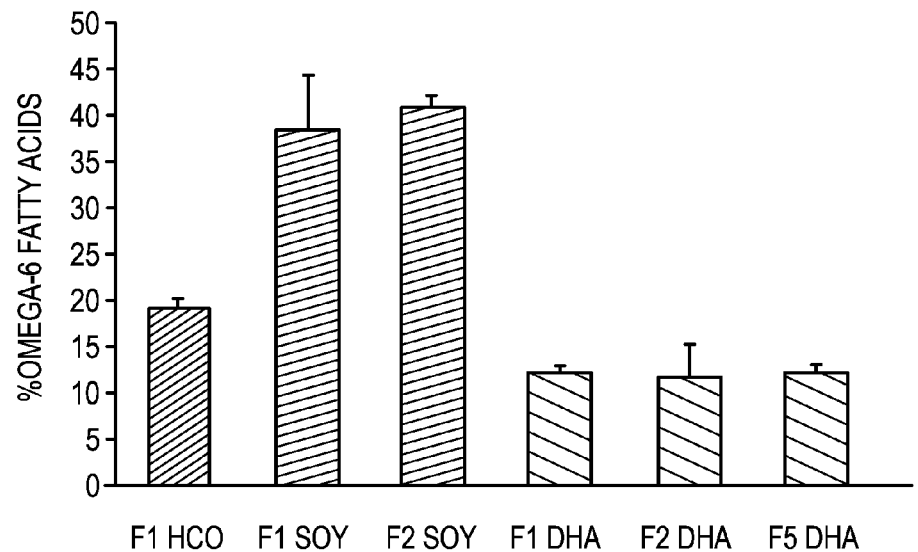
Figure 4D:
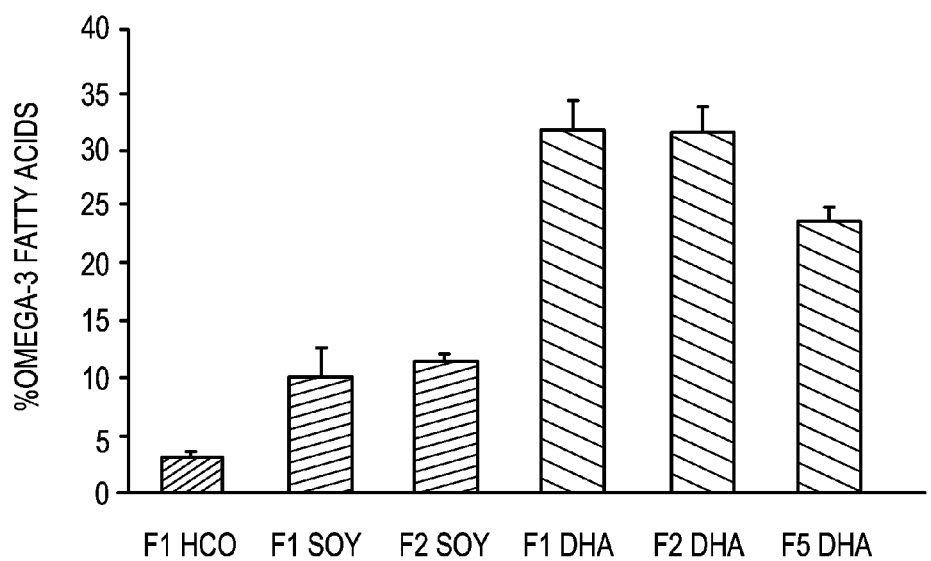

The dietary treatments did significantly change the fatty acid profiles of the serum resulting in a lower omega-6/omega-3 fatty acid ratio in the DHA group compared to the SOY and HCO groups (see FIGS. 4B-4D, demonstrating that serum omega-6/omega-3 fatty acid ratios (FIG. 4B) and the total percent of fatty acid attributable to (FIG. 4C) omega-6 and (FIG. 4D) omega-3 fatty acids differed significantly between groups. All data represented as mean±SD). Interestingly, the serum omega-6/omega-3 fatty acid ratio in the SOY diet group (3.98±0.48 for F1 and 3.62±0.12 for F2) was very similar to the ratio reported for humans consuming a typical Western diet (4.72±0.19) (Ambring A, Johansson M, Axelsen M, Gan L, Strandvik B, Friberg P (2006). Mediterranean-inspired diet lowers the ratio of serum phospholipid n-6 to n-3 fatty acids, the number of leukocytes and platelets, and vascular endothelial growth factor in healthy subjects. *Am J Clin Nutr.* 83, 575-581), indicating that this experimental diet does effectively mimic the serum omega-6 and omega-3 fatty acid distribution seen in Western societies.

Growth

Figure 4E:
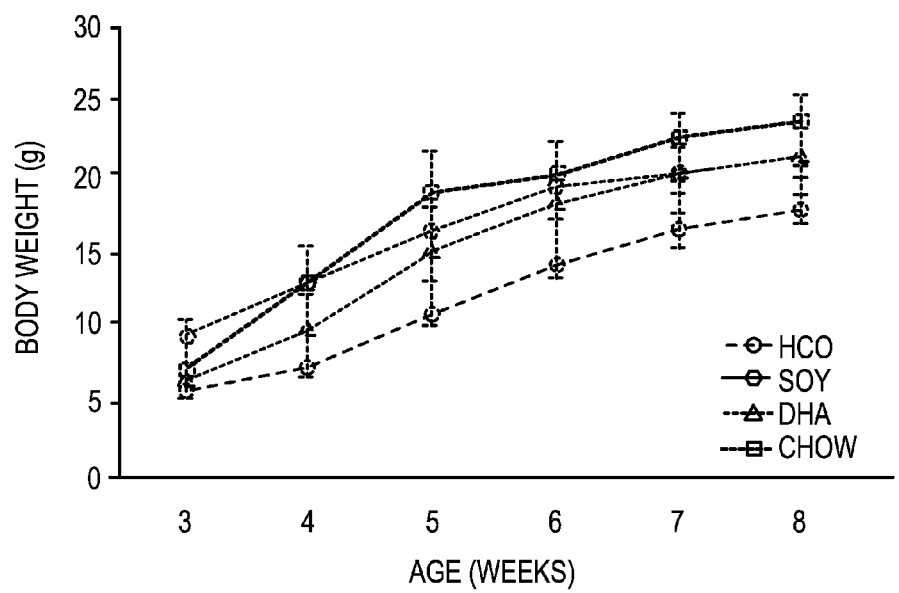
Figure 4F:
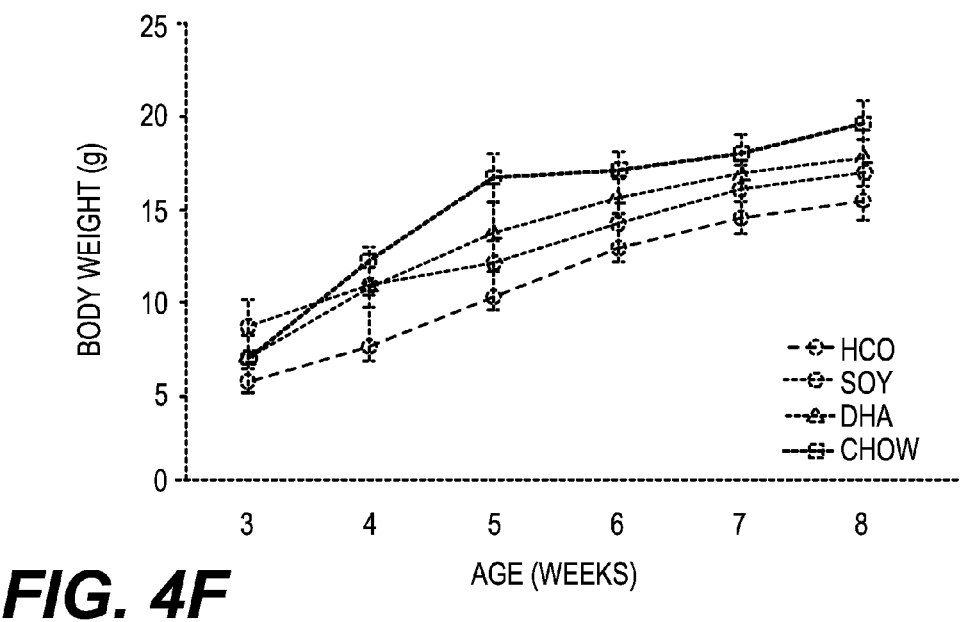
Figure 4G:
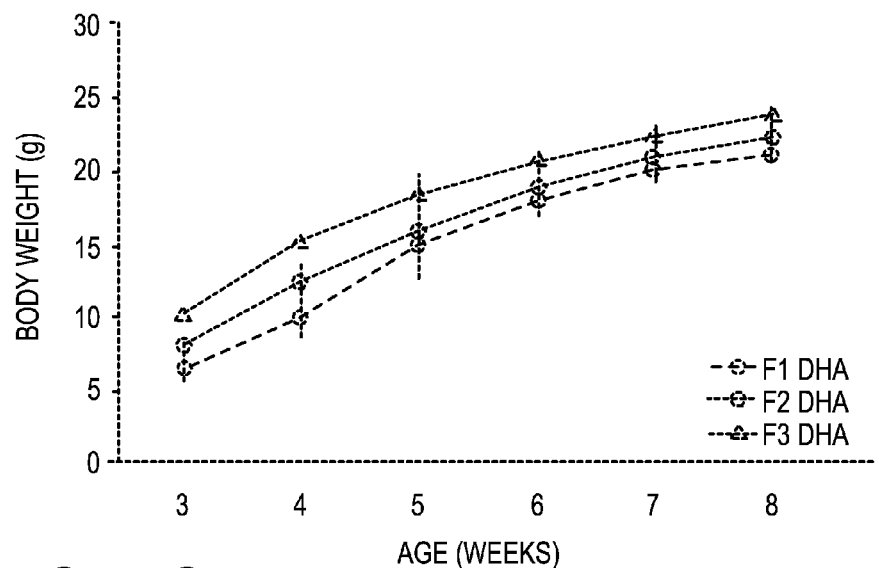
Figure 4H:
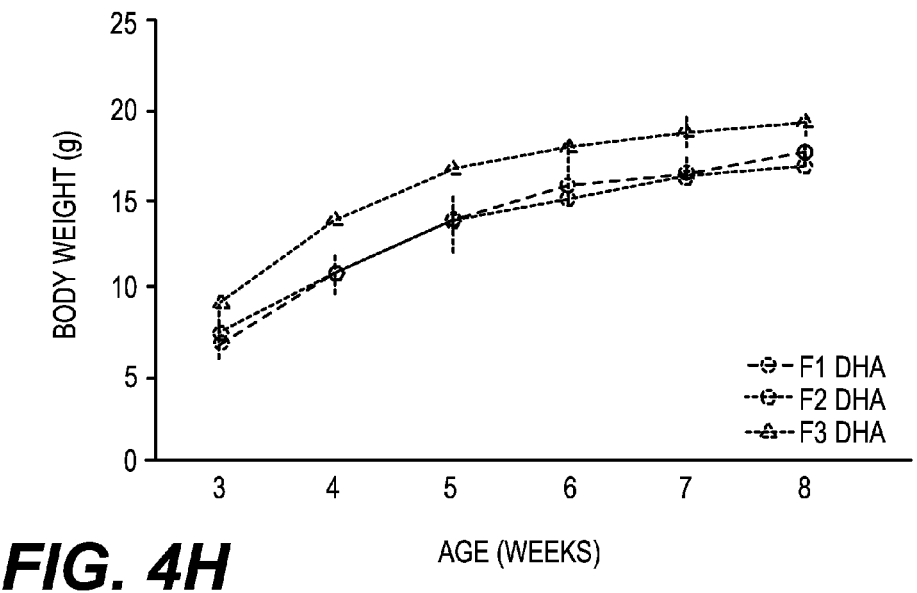

Animal weights were monitored for F1 generation animals on each of the experimental diets (HCO, SOY and DHA) and compared to age-matched animals on a standard laboratory rodent chow to provide a point of reference. There were no differences in the growth patterns of the SOY and DHA animals from weaning to adulthood when compared with the standard laboratory rodent chow-fed animals. Animals on the HCO diet had retarded growth evidenced by consistently lower weekly weights than animals on the other diets, a difference that was more pronounced for males than for females (see FIGS. 4E-4F, demonstrating that weekly average body weight of representative F1 generation (FIG. 4E) males and (FIG. 4F) females from week 3 (wean) to week 8 of life. Weekly body weights did not differ between animals on the CHOW, SOY and DHA diets but were consistently lower for animals on the HCO diet (N=5, 11, 7, 5 male and N=5, 6, 9, 5 female animals for CHOW, HCO, SOY and DHA diet groups, respectively). All data represented as mean±SD.). Successive generations of animals on the DHA diet were monitored to ensure normal growth patterns in later generations of animals, and among these, no differences were noted in the growth of F2 and F5 generation animals (see FIGS. 4G-4H, demonstrating that weekly average body weight of representative F1, F2 and F5 generation (FIG. 4G) males and (FIG. 4H) females from week 3 (wean) to week 8 of life. Animals on the DHA diet continued to demonstrate normal growth despite lifelong treatment with this diet over multiple generations (N=5, 8, 6 male and N=5, 5, 6 female animals for F1, F2 and F5 DHA groups, respectively). All data represented as mean±SD.) compared to the F1 generation. This indicates that even the lifelong consumption of this omega-3 fatty acid rich diet over multiple generations is not associated with any detrimental effect of growth.

Histology

Hematoxylin and eosin stained slides of the brain, heart, lung, liver, kidney, spleen and femur from a total of 15 adult F5 generation animals were reviewed by a rodent pathologist. These were compared to hematoxylin and eosin stained slides of the same organs from 5 age-matched animals on a standard rodent chow. No abnormalities were noted on review of the brain, heart, liver, kidney and femur specimens. Three of the 15 lung samples from animals on the DHA diet had mild emphysematous changes, potentially a result of trauma during the harvest and preservation. Additionally, 4 animals on the DHA diet had mild extramedullary hematopoiesis in the spleen, a non-specific finding in the laboratory mouse.

Discussion

Described herein is evidence that administration of omega-3 fatty acids (e.g. by dietary consumption) not only prolong the reproductive lifespan but also result in a remarkable improvement in egg quality in a murine model. These findings relate to both successful natural and assisted reproduction at advanced maternal age.

It is demonstrated herein that mice on an omega-3 fatty acid rich diet are able to successfully reproduce well beyond the normal expected reproductive lifespan for these animals. Although the average litter was slightly smaller (4.4±1.9 offspring/litter) for dams at advanced maternal age (>10 months) on the omega-3 rich diet compared to younger cohorts of animals (6.0±2.7 offspring/litter) on the same diet, the survival of the offspring born to dams at advanced maternal age was remarkably high at 89%. In stark contrast, aged animals (>10 months) maintained on a standard laboratory rodent chow or an omega-6 fatty acid rich diet (designed to mimic the typical Western diet) had extremely poor reproductive success. These may indicate that the increase in dietary omega-6 fatty acids in the human diet over the last 100 years may actually be detrimental to the reproductive success of women of advanced maternal age.

However, some subject may not be amendable to lifelong consumption of a diet containing a very high omega-3 to omega-6 fatty acid ratio as a feasible strategy for prolonging the natural reproductive lifespan. An alternative approach includes dietary changes that women who desire to delay childbearing could initiate at the time of, or immediately prior to, the presumed time of the natural decline in reproductive fertility. The data described herein indicated that the institution of a diet rich in omega-3 fatty acids around the time of the expected rapid decline in natural fertility results in a remarkable improvement in oocyte quality as measured by mitochondrial dynamics and the structure of the spindle apparatus. Egg quality is recognized as the single most important factor for determining the success of pregnancy for women of advanced reproductive age (Navot D, Bergh P A, Williams M, Garrisi G J, Guzman I, Sandler B, Fox J, Schreiner-Engel P, Hofmann G E, Grunfeld L (1991a). An insight into early reproductive processes through the in vivo model of ovum donation. *J Clin Endocrinol Metab.* 72, 408-414; Navot D, Bergh P A, Williams M A, Garrisi G J, Guzman I, Sandler B, Grunfeld L (1991b). Poor oocyte quality rather than implantation failure as a cause of age-related decline in female fertility. *Lancet.* 337, 1375-1377). With advanced age, the meiotic cell cycle of the egg becomes prone to errors of chromosomal segregation, which results in a much higher proportion of aneuploidy in oocytes ovulated by older women (Hunt P A (1998). The control of mammalian female meiosis: factors that influence chromosome segregation. *J Assist Reprod Genet.* 15, 246-252; Hassold T, Hunt P (2009). Maternal age and chromosomally abnormal pregnancies: what we know and what we wish we knew. *Curr Opin Pediatr.* 21, 703-708). Strategies to improve the quality of oocytes in aged animal models are limited. Chronic antioxidant treatment has been shown to counteract the negative effects of female aging on oocyte quality (Tarin J J, Perez-Albala S, Cano A (2002a). Oral antioxidants counteract the negative effects of female aging on oocyte quantity and quality in the mouse. *Mol Reprod Dev.* 61, 385-397); however, this treatment has not been shown to improve reproductive success and the clinical application is not feasible due to very significant negative effects on ovarian and uterine function (Tarin J J, Perez-Albala S, Pertusa J F, Cano A (2002b). Oral administration of pharmacological doses of vitamins C and E reduces reproductive fitness and impairs the ovarian and uterine functions of female mice. *Theriogenology.* 57, 1539-1550). Adult onset caloric restriction has been shown to sustain the function of the murine female reproductive axis into advanced chronological age with one half of calorically restricted animals remaining fertile for 6 months beyond the time at which control animals experienced a loss of fertility with a 73% survival for pups born to these dams at advanced maternal age (Selesniemi K, Lee H J, Tilly J L (2008). Moderate caloric restriction initiated in rodents during adulthood sustains function of the female reproductive axis into advanced chronological age. *Aging Cell.* 7, 622-629). This caloric restriction strategy has also been shown to improve oocyte quality (Simopoulos A P (2011). Importance of the omega-6/omega-3 balance in health and disease: evolutionary aspects of diet. *World Rev Nutr Diet.* 102, 10-21) although, the clinical application remains limited due to the expected deleterious health effects associated with the very severe caloric restriction necessary to obtain these beneficial effects. The data described herein indicate that dietary omega-3 fatty acids can protect against the age-related decline in oocyte quality, thus providing an avenue for women of advanced reproductive age to successfully conceive and deliver viable offspring. In addition, the potential for improving oocyte quality and thus decreasing the aneuploidy rate in women of advanced reproductive age indicates the methods described herein can reduce the occurrence of chromosomal disorders such as Down's Syndrome.

The omega-3 fatty acid rich diet associated with the beneficial reproductive effects in this study provided 2% of total calories in the form of the omega-3 fatty acid DHA. Prior studies do suggest that even very high doses of the omega-3 fatty acids DHA and eicosapentaenoic acid (EPA; 20:5n-3) are well tolerated and can be safely administered to both pediatric and adult patients (Lloyd-Still J D, Powers C A, Hoffman D R, Boyd-Trull K, Lester L A, Benisek D C, Arterburn L M (2006). Bioavailability and safety of a high dose of docosahexaenoic acid triacylglycerol of algal origin in cystic fibrosis patients: a randomized, controlled study. *Nutrition.* 22, 36-46; Sorgi P J, Hallowell E M, Hutchins H L, Sears B (2007). Effects of an open-label pilot study with high-dose EPA/DHA concentrates on plasma phospholipids and behavior in children with attention deficit hyperactivity disorder. *Nutr J.* 6, 16; Gura K M, Lee S, Valim C, Zhou J, Kim S, Modi B P, Arsenault D A, Strijbosch R A, Lopes S, Duggan C, Puder M (2008). Safety and efficacy of a fish-oil-based fat emulsion in the treatment of parenteral nutrition-associated liver disease. *Pediatrics.* 121, e678-686). Additionally, it is well recognized that the beneficial effects of dietary omega-3 fatty acids are determined by both the ratio of omega-3 to omega-6 fatty acids in the diet and the absolute doses of these fatty acids (Simopoulos A P (2002). The importance of the ratio of omega-6/omega-3 essential fatty acids. *Biomed Pharmacother.* 56, 365-379). Thus, in some embodiments, the methods described herein can relate to, for example, pharmacologic doses of omega-3 fatty acids in addition to limiting the omega-6 fatty acid content in the diet.

In addition to the beneficial effects of omega-3 fatty acids on murine reproductive function, described herein is evidence that at least DHA and AA may be a sufficient source of fat for the maintenance of life and the prevention of essential fatty acid deficiency. About 80 years ago, ALA and LA were determined by Burr and Burr to be the essential fatty acids necessary for healthy skin and successful growth, reproduction and lactation (Burr G O, Burr M M (1973). Nutrition classics from The Journal of Biological Chemistry 82:345-67, 1929. A new deficiency disease produced by the rigid exclusion of fat from the diet. *Nutr Rev.* 31, 248-249). DHA and AA are downstream molecules in the omega-3 and omega-6 fatty acid pathways, respectively, that have been identified having roles in numerous physiological and biochemical processes. The data described herein demonstrate that a diet containing a 20:1 ratio of DHA:AA, is safe for long-term consumption with no appreciable adverse health effects in a murine model. Animals on this diet for over 6 generations consistently had very low T:T ratios and mead acid levels, suggesting the absence of biochemical essential fatty acid deficiency. These animals had no evidence of clinical essential fatty acid deficiency with maintenance of skin health and normal growth, reproduction and lactation.

The data described herein demonstrate that the consumption of omega-3 fatty acids improves reproductive success at advanced maternal age. Also provided is evidence that oocyte quality is improved in animals consuming an omega-3 rich diet. can include the maintenance of reproductive potential in women considered to be of advanced maternal age.

This study has uncovered a beneficial effect of a diet rich in omega-3 fatty acids on murine reproductive success and oocyte quality at ages normally associated with poor reproductive parameters. A diet rich in omega-3 fatty acids, for example, comprising 2.1% of total calories provided as a 20:1 ratio of DHA:AA, was found to be safe for consumption over several generations and with an improvement in natural fertility at advanced age. The acute dietary treatment of animals during the time of the naturally occurring steep decline in reproductive potential results in improved oocyte quality as measured by the structure of the spindle apparatus and mitochondrial dynamics.

Experimental Procedures

All animal husbandry and experimental procedures were reviewed and approved by the institutional animal care and use committee of Children's Hospital Boston. All animals were housed on paper chip bedding in a barrier room with regulated temperature (21° C.±1.6° C.), humidity (45%±10%), and an alternating 12-hour light and dark cycle with ad libitum access to water and study diets.

Long-Term Diet Studies (Reproduction and Fertility)

Animals.

Virgin C57BL/6 adult female mice and adult male C57BL/6 mice were obtained from Jackson Laboratories (#000664; Jackson Laboratories, Bar Harbor, Me., USA).

Male fertility was confirmed prior to breeding trials and no males older than the age of 6 months were used for any breeding trials.

Feeding Regimen.

Adult female animals were randomized to 1 of 3 different diet groups each containing 10% of total calories in the form of fat provided as either: soybean oil (SOY; #110990, Dyets Inc., Bethlehem, Pa., USA), hydrogenated coconut oil (HCO; #102328, Dyets Inc., Bethlehem, Pa., USA) or a 20:1 ratio of DHA:AA (DHA; #102536, Dyets Inc., Bethlehem, Pa., USA). The detailed composition of each diet is shown in Table 1.

The initial animals were termed the F0 generation and these animals remained on their respective diets for 4 weeks prior to the initiation of breeding trials. Subsequent generations of animals were maintained on the same diet as their mother for their entire lifetime. Males were rotated between cages such that no male consumed any particular diet for longer than 1 week.

Breeding Trials.

After 4 weeks of dietary treatment, breeding trials were initiated with F0 animals in each of the diet groups. The offspring were termed the F1 generation. After reaching reproductive maturity, the F1 animals were bred to generate an F2 generation and subsequent breeding trials were continued to the F3 generation for the SOY animals and the F6 generation for the DHA animals. Animals on the HCO diet were unable to successfully breed beyond the F1 generation. The total number of offspring delivered per litter and the number of offspring delivered that were viable (survived to wean) were recorded separately for each pregnancy. Offspring that did not survive were either found dead at birth or died very shortly thereafter. All viable offspring were allowed to remain with the dam until wean (post-partum day 21), at which time the offspring were removed from the cages to allow for subsequent mating attempts with the dam. All male offspring were euthanized and a subset of randomly selected females from each generation was kept for further breeding.

Breeding trials at advanced murine reproductive age, defined as age >10 months, were continued on a subset of F2 and F3 female animals in the SOY (N=10) and DHA (N=7) diet groups. To provide a comparison, breeding trials were concomitantly initiated on age-matched female animals on a standard laboratory rodent chow (CHOW; National Institute on Aging, Bethesda, Md., USA). Breeding trials were conducted exactly as described above except that viable offspring were allowed to remain with the dam until post-partum day 14, at which time the offspring were euthanized and subsequent mating attempts with the dam were continued. Breeding trials were continued in this fashion until the dam reached 15-months of age.

Acute Dietary Treatment Studies (Oocyte Quality)

Animals.

Virgin female C57BL/6 mice were obtained from the National Institute on Aging (NIA, Bethesda, Md., USA) at the age of 10 months. These animals were fed the NIH-31 standard laboratory rodent chow from birth to time of purchase.

Feeding Regimen.

Female animals were randomized to 1 of 3 different diet groups (N=12/group): CHOW, SOY and DHA. The amount of diet consumed and the growth of each animal were monitored on a weekly basis. All animals received the experimental diet until euthanasia at 13 months of age, equating to 12 weeks of dietary treatment.

Fatty Acid Profiles.

Serum fatty acid profiles were performed on 5 representative serum samples from animals in each of the diet groups. Total fatty acids were extracted per the modified Folch method (Folch J, Lees M, Sloane Stanley G H (1957). A simple method for the isolation and purification of total lipids from animal tissues. *J Biol. Chem.* 226, 497-509). Fatty acid analysis was performed on a Hewlett-Packard 6890N gas chromatograph (GMI Inc., Ramsey, M N, USA) coupled to an HP-5975B mass spectrometer equipped with Supelcowax SP-10 capillary column (GMI Inc., Ramsey, M N, USA). Fatty acid concentrations (nmol/mL serum) were calculated by proportional comparison of peak areas to the area of the 17:0 internal standard.

Oocyte Retrieval.

Mice (N=12 CHOW, N=11 SOY, N=12 DHA) were superovulated with an intraperitoneal injection of pregnant mare serum gonadotropin (PMSG, 10 IU; Sigma-Aldrich, St. Louis, Mo., USA) followed by human chorionic gonadotropin (hCG, 10 IU; Sigma-Aldrich, St. Louis, Mo., USA) 48 hours later. Oocytes were collected from oviducts 15-16 hours after hCG injection by puncturing the oviducts with an insulin syringe. Retrieved oocytes were denuded of cumulus cells by a brief incubation in 801 U/mL of hyaluronidase (Sigma-Aldrich, St. Louis, Mo., USA), followed by 3 washes with human tubal fluid (HTF) (Irvine Scientific, Santa Ana, Calif., USA) supplemented with 0.4% BSA (fraction V, fatty acid free; Sigma-Aldrich, St. Louis, Mo., USA). Oocytes were counted and classified using a Hoffman light microscope as mature metaphase II (MII; presence of first polar body in perivitelline space), maturation arrested (germinal vesicle breakdown with no polar body extrusion, or germinal vesicle intact), or dead (condensed, fragmented cytoplasm). Oocytes from the 3 diet groups were analyzed in parallel.

Mitochondrial Analysis.

A subset of mature (MII) oocytes collected from each diet group were denuded of adherent somatic (cumulus) cells and incubated in HTF medium supplemented with 0.4% BSA and 200 nM MitoTracker Red CMRox (Life Technologies, Grand Island, N.Y., USA) for 60 minutes at 37° C. Oocytes were washed and incubated in acidified Tyrode's solution (Irvine-Scientific, Santa Ana, Calif., USA), washed, fixed, and washed again followed by an incubation in phosphate buffered saline (PBS; Sigma-Aldrich, St. Louis, Mo., USA) containing 0.5% BSA, 0.05% Tween-20 (Sigma-Aldrich, St. Louis, Mo., USA), and 0.1% Triton X-100 (Sigma-Aldrich, St. Louis, Mo., USA) for 1 hour. Oocytes were then mounted using Vectashield (Vector Laboratories, Burlingame, Calif., USA) and analyzed by confocal microscopy by 2 independent trained observers. Oocytes with a uniform cytoplasmic distribution of active mitochondria were scored as normal.

DNA and Spindle Apparatus Analysis.

A subset of mature (MII) oocytes collected from each diet group were washed in PBS containing 0.5% BSA and briefly incubated in acidified Tyrode's solution to soften and remove the zona pellucida. The oocytes were then washed and fixed in 2.0% neutral-buffered paraformaldehyde containing 0.5% BSA. Permeabilization and blocking was performed by incubating the oocytes in mouse blocking solution (Vector Laboratories, Burlingame, Calif., USA) supplemented with 0.5% BSA, 0.1% Triton-X, 0.05% Tween-20, and 5% normal goat serum (Vector Laboratories, Burlingame, Calif., USA). Oocytes were washed and incubated overnight in a 1:200 dilution of mouse anti-α-tubulin antibody (Sigma-Aldrich, St. Louis, Mo., USA) in PBS containing 0.5% BSA, washed and incubated with a 1:250 dilution of goat antimouse IgG conjugated with Alexa Fluor-488 (Life Technologies, Grand Island, N.Y., USA). Following washing, oocytes were mounted using Vectashield containing propidium iodide (Vector Laboratories, Burlingame, Calif., USA) and analyzed by confocal microscopy. For the spindle analysis, oocytes with barrel-shaped bipolar spindles having distinct and well-organized microtubule fibers, along with tightly aligned chromosomes on the metaphase plate, were scored as normal. Oocytes from the 3 groups were analyzed in parallel.

Ovarian Follicle Counts.

Ovaries were fixed, paraffin embedded, serially sectioned (8 μm) and aligned in order on glass microscope slides. The sections were then stained with hematoxylin and picric methyl blue, and analyzed for the number of non-atretic primordial, primary and small preantral follicles in every other section with a random start, as previously described (Morita Y, Perez G I, Maravei D V, Tilly K I, Tilly J L (1999). Targeted expression of Bcl-2 in mouse oocytes inhibits ovarian follicle atresia and prevents spontaneous and chemotherapy-induced oocyte apoptosis in vitro. *Mol. Endocrinol.* 13, 841-850). Only those follicles containing an oocyte with a clearly visible nucleus were scored. Given that this procedure samples one-half of the entire ovarian volume, the total number of follicles per ovary was then estimated by multiplying the cumulative counts for each ovary by a correction factor of 2. All counts were performed by a blinded study investigator.

Safety Evaluation

Fatty Acid Profiles.

Serum fatty acid profiles were performed on serum samples collected from randomly chosen animals. Representative samples were chosen to represent different generations of animals on the HCO, SOY and DHA diets. Serum was collected from the following representative animals: F1 HCO (n=4), F1 SOY (n=5), F2 SOY (N=5), F1 DHA (N=5), F2 DHA (N=4), F5 DHA (N=15) and fatty acid extraction and analysis were performed as described above.

Growth.

The growth of representative litters born to dams on each of the diets in the long-term diet arm of the study were monitored with serial weights obtained from wean to adulthood. Representative and randomly chosen F1 litters in the SOY and HCO groups and F1, F2 and F5 litters in the DHA group were monitored. Similarly, the weights of litters born to dams on a standard laboratory chow (CHOW) were also monitored to provide an additional point of reference.

Histologic Analysis.

Fifteen adult animals from the F5 generation on the DHA diet were euthanized for histologic analysis of the organ systems. Brain, heart, lung, liver, kidney, spleen and long bone (femur) from each of these animals was harvested, fixed in 10% formalin, embedded in paraffin and stained with hematoxylin and eosin. Comparison samples were obtained from 5 age-matched C57BL/6 mice on a standard laboratory rodent chow. All slides were reviewed by a rodent pathologist and were classified as either normal or abnormal based on the histologic appearance. Details regarding any notable abnormalities were recorded.

Statistical Analysis.

All continuous variables presented as mean±standard deviation (SD). Continuous variables were analyzed with the Student's t-test or, when the data was not normally distributed, the Mann-Whitney U test. Continuous variables from more than 3 independent groups were analyzed with the Kruskal-Wallis one-way analysis of variance. Categorical variables were analyzed with the chi-square test. Significance was assessed using a two-sided 5% alpha level. All statistical analysis was performed with the GraphPad Prism software (version 4.0; San Diego, Calif., USA).

What is claimed is:

1. A method for enhancing, improving, or increasing a female human's likelihood of becoming pregnant comprising:
    administering to the human a nutritional, dietary, or food fatty acid supplement comprising:
    at least 30% docosahexaenoic acid (DHA), by weight of the total fatty acids in the supplement in a form chosen from ethyl ester, free fatty acid, and triglyceride.

2. The method according to claim 1, wherein the supplement further comprises eicosapentaenoic acid (EPA) in a form chosen from ethyl ester, free fatty acid, and triglyceride.

3. The method according to claim 1 or 2, wherein the supplement further comprises arachidonic acid in a form chosen from ethyl ester, free fatty acid, and triglyceride.

4. The method of according to claim 1, wherein the DHA is in the form of triglyceride.

5. The method according to claim 1, wherein the supplement further comprises vitamin D.

6. The method according to claim 5, wherein the vitamin D is present in an amount ranging from about 400 to about 4000 International Units (IU), from about 1000 to about 4000 IU, or from about 2000 to about 4000 IU.

7. The method according to claim 5, wherein the supplement further comprises at least one vitamin other than vitamin D.

8. The method according to claim 2, wherein the weight ratio of the DHA to the EPA ranges from about 500:1, 100:1, 50:1, 20:1, 15:1, 10:1, 9:1, 8:1, 7:1, 6:1, 5:1, 4:1, 3:1, 2:1, to 1:1.

9. The method according to claim 3, wherein the weight ratio of the omega-3 fatty acids to the omega-6 fatty acids is about 10:1 or greater.

10. The method according to claim 9, wherein the weight ratio of the omega-3 fatty acids to omega-6 fatty acids is about 20:1, 21:1, 22:1, 23:1, 24:1, 25:1 or greater.

11. The method according to claim 2, wherein DHA is present in an amount greater than EPA.

12. The method according to claim 11, wherein DHA is present in an amount ranging from about 500 mg to about 750 mg, and EPA is present in an amount ranging from about 80 mg to about 250 mg.

13. The method according to claim 12, wherein DHA:EPA are present in a weight ratio chosen from about 70:10, 500:200, and 600-750:150-250.

14. The method according to claim 2, wherein the supplement comprises from about 650 mg to about 750 mg DHA and from about 80 mg to about 130 mg EPA.

15. The method according to claim 1, wherein the supplement comprises from about 750 mg to about 900 mg total omega-3 fatty acids.

16. The method according to claim 1, wherein the supplement further comprises at least one antioxidant.

17. The method according to claim 16, wherein the at least one antioxidant is chosen from α-tocopherol (vitamin E), calcium disodium EDTA, alpha tocoferyl acetates, butylhydroxytoluenes (BHT), butylhydroxyanisoles (BHA), ascorbic acid and pharmaceutically acceptable salts and esters thereof, propyl gallate, citric acid and pharmaceutically acceptable salts thereof, malic acid and pharmaceutically acceptable salts thereof, and sulfite salts and mixtures thereof.

18. The method according to claim 17, wherein the at least one antioxidant comprises BHA.

19. The method according to claim 1, wherein the total omega-3 fatty acids are at least 70%, at least 75%, at least 80%, or at least 90%, by weight of the total fatty acids in the supplement.

20. The method according to claim 2, wherein DHA and EPA are present in an amount chosen from about 35% to about 90% by weight of the total fatty acids in the supplement, from about 40% to about 85% by weight of the total fatty acids in the supplement, from about 40% to about 80% by weight of the total fatty acids in the supplement, and from about 50% to about 80% by weight of the total fatty acids in the supplement.

21. The method according to claim 1, wherein the supplement comprises at least one other fatty acid other than DHA in a form chosen from ethyl ester, free fatty acid, and triglyceride.

22. The method according to claim 2, wherein the supplement further comprises: eicosapentaenoic acid (EPA) in a form chosen from ethyl ester, free fatty acid, and triglyceride, wherein DHA is present in an amount greater than EPA; and arachidonic acid in a form chosen from ethyl ester, free fatty acid, and triglyceride, wherein the weight ratio of omega-3 fatty acids to omega-6 fatty acids is 10:1 or greater.

23. The method according to claim 1, wherein the daily dosage per day of the total fatty acids in the supplement ranges from 1 to 8 grams.

24. The method according to claim 1, wherein DHA is present in an amount of at least 90% by weight of the total fatty acids in the supplement.

25. The method according to claim 1 including maintaining or improving oocyte and/or ovum quality in a human in need thereof.

26. The method according to claim 1, wherein the oocyte and/or ovum quality is maintained or improved by decreasing the likelihood of abnormalities in at least one of spindle integrity and mitochondrial dynamics in the oocyte and/or ovum.

27. The method according to claim 1, wherein the oocyte and/or ovum quality is maintained or improved by decreasing the likelihood of at least one chromosomal abnormality in the oocyte and/or ovum.

28. The method according to claim 27, wherein the at least one chromosomal abnormality is chosen from 22q11.2 deletion syndrome, Angelman syndrome, Canavan disease, Coeliac disease, Charcot-Marie-Tooth disease, color blindness, Cri du chat, Cystic fibrosis, Down Syndrome, Duchenne muscular dystrophy, Haemochromatosis, Haemophilia, Klinefelter's syndrome, Neurofibromatosis, Phenylketonuria, Polycystic kidney disease, Prader-Willi syndrome, Sickle-cell disease, Tay-Sachs disease, and Turner syndrome.

29. The method according to claim 1, wherein the supplement is enterally or parenterally administered.

30. The method of claim 29, wherein the supplement is enterally administrated and the enteral administration is chosen from oral, gastric, and rectal.

31. The method according to claim 1, wherein the human is undergoing infertility treatment.

32. The method according to claim 1, including enhancing and/or prolonging fertility and/or reproductive function in a female human or animal in need thereof.

33. The method according to claim 1, including delaying the onset of menopause in a female human or animal in need thereof.

34. The method according to claim 1, the method comprising;
    administering the nutritional, dietary or supplement to a subject having a serum level ratio of omega-3 fatty acids to omega-6 fatty acids of 1:1 or less.

35. The method of claim 34, further comprising determining the serum level ratio of omega-3 fatty acids to omega-6 fatty acids after administering the nutritional, dietary or supplement; and
    administering additional doses of the nutritional, dietary or supplement comprising an omega-3 fatty acid when the subject is determined to have a serum level ratio of omega-3 fatty acids to omega-6 fatty acids of 1:1 or less.

36. The method of claim 35, further comprising determining the serum level ratio of omega-3 fatty acids to omega-6 fatty acids; and
    administering doses of the composition comprising an omega-3 fatty acid until the subject is determined to have a serum level ratio of omega-3 fatty acids to omega-6 fatty acids of greater than 1:1.

* * * * *